(12) United States Patent
Forsgren et al.

(10) Patent No.: US 7,470,432 B2
(45) Date of Patent: Dec. 30, 2008

(54) SURFACE EXPLOSED IMMUNOGLOBULIN D-BINDING PROTEIN FROM MORAXELLA CATARRHALIS

(75) Inventors: Arne Forsgren, Falsterbo (SE); Kristian Riesbeck, Malmö (SE); Håkan Jansson, Lund (SE)

(73) Assignee: Arne Forsgren et al, Falsterbo (SE)

( * ) Notice: Subject to any disclaimer, the term of this patent is extended or adjusted under 35 U.S.C. 154(b) by 388 days.

(21) Appl. No.: 10/480,456

(22) PCT Filed: Jul. 1, 2002

(86) PCT No.: PCT/SE02/01299

§ 371 (c)(1),
(2), (4) Date: Jul. 13, 2004

(87) PCT Pub. No.: WO03/004651

PCT Pub. Date: Jan. 16, 2003

(65) Prior Publication Data

US 2005/0027104 A1 Feb. 3, 2005

(30) Foreign Application Priority Data

Jul. 4, 2001 (SE) .................................... 0102410

(51) Int. Cl.
*A61K 39/02* (2006.01)
(52) U.S. Cl. .............. 424/251.1; 424/185.1; 424/190.1; 424/192.1; 435/4; 435/7.32
(58) Field of Classification Search .............. 424/251.1, 424/185.1, 190.1, 192.1; 435/4, 7.32
See application file for complete search history.

(56) References Cited

U.S. PATENT DOCUMENTS 5,808,024 A * 9/1998 Sasaki et al. ................ 536/23.1

6,214,981 B1 * 4/2001 Tucker et al. .............. 536/23.1
6,673,910 B1 * 1/2004 Breton ....................... 536/23.1

FOREIGN PATENT DOCUMENTS

| WO | WO 96/34960 | 11/1996 |
| WO | WO 01/05424 | 1/2001 |
| WO | WO 01/07619 | 2/2001 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp -7).*
(Murphy et al. Pediatr. Infect. Dis. J. 1989. 8: S66-S68).*
Yamanaka et al (J. Pediatrics. 1993. 122(2): 212-218).*
Arne Forsgren et al., "Isolation and Characterization of Novel IgD-Binding Protein from *Moraxella catarrhalis*", The Journal of Immunology, vol. 167, 2001, pp. 2112 to 2120.
Arne Forsgren et al., "*Branhamella catarrhalis* Activates Human B Lymphocytes Following Interactions with Surface IgD and Class 1 Major Histocompatibility Complex Antigens", Cellular Immunology, vol. 112, 1988, pp. 78 to 88.
Thomas F. Tedder, "Immunoglobulin D-Binding Bacteria", Bacterial Immunoglobulin-Binding Proteins, vol. 1, 1990, pp. 235 to 242.

* cited by examiner

*Primary Examiner*—Jennifer E. Graser
(74) *Attorney, Agent, or Firm*—Buchanan Ingersoll & Rooney PC

(57) ABSTRACT

The present invention relates to a surface exposed protein, which can be detected in *Moraxella catarrhalis*, having an amino acid sequence as described in SEQ ID NO 1, an apparent molecular weight of 200 kDa and a capacity of selectively binding membrane bound or soluble IgD, to an immunogenic or IgD-binding fragment of said surface exposed protein, and to an immunogenic and adhesive fragment of said surface exposed protein. DNA segments, vaccines, plasmids and phages, non human hosts, recombinant DNA molecules and plants, fusion proteins and polypeptides and fusion products are also described. A method of detecting IgD, a method of separating IgD, a method of isolation of a surface exposed protein of *Moraxella catarrhalis* and a method for treatment of an autoimmune disease are also disclosed.

3 Claims, 28 Drawing Sheets

```
-250
ACTCTATTATTTGATATGTTTTGAAACTAATCTATTGACTTAAATCACCATATGGTTATAAT

TTAGCATAATGGTAGGCTTTTTGTAAAAATCACATCGCAATATTGTTCTACTGTTACTACCA
    -35
TGCTTGAATGACGATCCCAATCATCAGATTCATTCAAGTGATGTGTTTGTATACGCATCATT
      -10                                                  rbs
TACCCTAATTATTTCAATCGAAATGCCTATGTCAGCATGTATCATTTTTTTAAGGTAAACCA
   1/1                                   31/11
CC ATG AAT CAC ATC TAT AAA GTC ATC TTT AAC AAA GCC ACA GGC ACA
   Met asn his ile tyr lys val ile phe asn lys ala thr gly thr
                     61/21
TTT ATG GCC GTG GCG GAA TAT GCC AAA TCC CAC AGC ACG GGG GGT
phe Met ala val ala glu tyr ala lys ser his ser thr gly gly
91/31                                              121/41
AGC TGT GCT ACA GGG CAA GTT GGC AGT GTA TGC ACT CTG AGC TTT
ser cys ala thr gly gln val gly ser val cys thr leu ser phe
                 151/51
GCC CGT GTT GCC GCG CTC GCT GTC CTC GTG ATC GGT GCG ACG CTC
ala arg val ala ala leu ala val leu val ile gly ala thr leu
181/61                                            211/71
AAT GGC AGT GCT TAT GCT CAA CAA GAT CCC AGA CAT ATC GCA ATT
asn gly ser ala tyr ala gln gln asp pro arg his ile ala ile
                   241/81
GAT GGC AAC AGC TCG AAC ACA TCC TCA GGC ACT GCC CGT GCG ACA
asp gly asn ser ser asn thr ser ser gly thr ala arg ala thr
271/91                                             301/101
GGT GAT CGA GCC ATT GCT CTT GGT GAA AAT GCT AAT GCA GAG GGC
gly asp arg ala ile ala leu gly glu asn ala asn ala glu gly
                    331/111
GGT CAA GCC ATC GCC ATC GGT AGT AGC AAT AAA ACA GGT GGT AGA
gly gln ala ile ala ile gly ser ser asn lys thr gly gly arg
361/121                                            391/131
AAC GCG CTG AAT ATA GGT ACC GAT GCC AAA GGT GAG GAG TCC ATC
asn ala leu asn ile gly thr asp ala lys gly glu glu ser ile
                    421/141
GCC ATC GGT GGT GAT GTA GTG GCT GAG GGT ACT GCC TCG ATT GCC
ala ile gly gly asp val val ala glu gly thr ala ser ile ala
451/151                                            481/161
ATC GGT GGT GAT GAC TTA CAT TTG TGG GAT GAA CCA AAT AAG CAA
ile gly gly asp asp leu his leu trp asp glu pro asn lys gln
```

Fig 6

```
                    511/171
AAG TTC CTC GAC CCA AAA GTT AAA GAA TTG ATT TTA AAA CAT CAA
lys phe leu asp pro lys val lys glu leu ile leu lys his gln
541/181                                         571/191
GAA TTA AAC AAC ATA TAC AAA CTG CCT GAT GGT AGT CCT CAA AGA
glu leu asn asn ile tyr lys leu pro asp gly ser pro gln arg
                            601/201
TAT TTT CGC ACA TAC GCA AAG GGA CAC GCC AGT ATT GCA CTA GGA
tyr phe arg thr tyr ala lys gly his ala ser ile ala leu gly
631/211                                         661/221
ACC ATG ACA CAG GCA GAG GGT CAT TTT GCC AAC GCC TTT GGT ACA
thr met thr gln ala glu gly his phe ala asn ala phe gly thr
                            691/231
CGG GCA ACA GCT AAA GGC AAC TAT TCC TTG GCA GTG GGT CTT ACC
arg ala thr ala lys gly asn tyr ser leu ala val gly leu thr
721/241                                         751/251
GCC CAA GCC AAC ACA GAA TCT TCA ATC GCT GTT GGT TCT AAT GCA
ala gln ala asn thr glu ser ser ile ala val gly ser asn ala
                            781/261
CAA GCT AAC GGG TTT GCA GCG ACA GCC ATT GGT GGA GGT ACT AAA
gln ala asn gly phe ala ala thr ala ile gly gly gly thr lys
811/271                                         841/281
GCT GAT TTG GGT CGA AGC ATA GCC CTA GGT TTT GGT TCT CAG ATC
ala asp leu gly arg ser ile ala leu gly phe gly ser gln ile
                            871/291
CTT ACT AAG GAG AAG GAT AGT CAT AAC AAT ACC AAT GTC TAT GTA
leu thr lys glu lys asp ser his asn asn thr asn val tyr val
901/301                                         931/311
CCA CAA GGT GAA ATA TTA GAA GAG CGG TAT AAA GCC ACC GAA AAC
pro gln gly glu ile leu glu glu arg tyr lys ala thr glu asn
                            961/321
GGT CAG TCG CCT AAT AAG GTA GTG GAT ATA TTT TCC ATT GGT AGT
gly gln ser pro asn lys val val asp ile phe ser ile gly ser
991/331                                         1021/341
AGC TCT ATC AAA CGT AAA ATC ATC AAT GTC GGT GCG GGT TCT CAG
ser ser ile lys arg lys ile ile asn val gly ala gly ser gln
                            1051/351
GAG ACC GAT GCG GTC AAT GTG GCA CAG CTT AAA TTG GTG GAG CGG
glu thr asp ala val asn val ala gln leu lys leu val glu arg
```

Fig 6 cont

```
1081/361                                    1111/371
GTG GCT AAG CGT CAA ATT ACT TTT CAG GGT GAT GAT AGC AAT AAT
val ala lys arg gln ile thr phe gln gly asp asp ser asn asn
                         1141/381
AGC GTA AAA AAA GGT TTG GGT CAG ACT TTA ACT ATT AAA GGT GGT
ser val lys lys gly leu gly gln thr leu thr ile lys gly gly
1171/391                                    1201/401
AAA ACA GAG ACC GGT GAA CTA ACC GAA AAT AAC ATC GGT GTG GTA
lys thr glu thr gly glu leu thr glu asn asn ile gly val val
                         1231/411
CAA GAT GAT AAT GGT AAT GGT CTG AAA GTT AAA CTT GCT AAA GAT
gln asp asp asn gly asn gly leu lys val lys leu ala lys asp
1261/421                                    1291/431
CTG ACT GGT TTG ACC AAG GTT GCA GTA AAT GGT AAT GGT GCT AAC
leu thr gly leu thr lys val ala val asn gly asn gly ala asn
                         1321/441
AAC GCC GAG CTA CTA AAC GGT GGT CTG ACC TTT TCG ACA TCA GGT
asn ala glu leu leu asn gly gly leu thr phe ser thr ser gly
1351/451                                    1381/461
GCC AAT GCA GGC AAA ACG GTC TAT GGC ACT GAT GGG GTG AAG TTT
ala asn ala gly lys thr val tyr gly thr asp gly val lys phe
                         1411/471
ACT AAT AAT ACA GGA ACA GGA ACA GGA ACG GCA ATA CCC GAC ACT
thr asn asn thr gly thr gly thr gly thr ala ile pro asp thr
1441/481                                    1471/491
ACT CGT ATT ACC AAA AAT AAA ATT GGC TTT GCT GGG GCT GAT GAA
thr arg ile thr lys asn lys ile gly phe ala gly ala asp glu
                         1501/501
CAA GTT GAT GAA AGC AAA CCT TAT CTT GAC AAC GAA AAG CTA AAA
gln val asp glu ser lys pro tyr leu asp asn glu lys leu lys
1531/511                                    1561/521
GTT GGC ACA GTT GAG ATT AAA AAA ACT GGC ATC AAT GCA GGT AAT
val gly thr val glu ile lys lys thr gly ile asn ala gly asn
                         1591/531
CAA GAA ATT ACC AAG GTC AAA TCT GCC ATT GTT GAT GCA GTT AAT
gln glu ile thr lys val lys ser ala ile val asp ala val asn
1621/541                                    1651/551
GGA CAA GCA AAT CAA AGC TTT GTG AAC CTT CTA GAA ACA GCA GGC
gly gln ala asn gln ser phe val asn leu leu glu thr ala gly
                         1681/561
ACA AAC ACC AAC AAA CAA AAC TCT GCC GCC ACG GTT AAA GAC TTA
thr asn thr asn lys gln asn ser ala ala thr val lys asp leu
```

Fig 6 cont

```
1711/571                                  1741/581
TAC GAC CTA TCA CAA TCA CCG CTG ACC TTT ACA GGT GAT AGC GGT
tyr asp leu ser gln ser pro leu thr phe thr gly asp ser gly
                        1771/591
AAC GTT AAG AGA AAA CTG GGT CAG ACT TTA ACC ATC ACA GGC GGA
asn val lys arg lys leu gly gln thr leu thr ile thr gly gly
1801/601                                  1831/611
CAA ACA AAG ACC GAT CAA TTA ACC GAC AAT AAC ATC GGT GTG GTA
gln thr lys thr asp gln leu thr asp asn asn ile gly val val
                        1861/621
GCA GGT ACT AAT GGC TTA ACC GTT AAA CTT GCT AAA ACT TTA AAC
ala gly thr asn gly leu thr val lys leu ala lys thr leu asn
1891/631                                  1921/641
AGT CTT ACT GAA GTT AAT ACG GCT ACA TTA AAC GCC ACC AAT AAA
ser leu thr glu val asn thr ala thr leu asn ala thr asn lys
                        1951/651
GTT AAG GTA GAT AAT AGT ACT GGT AAT ACG GCT GAA TTA TTA AAC
val lys val asp asn ser thr gly asn thr ala glu leu leu asn
1981/661                                  2011/671
AAT GGT TTA ACC TTT ACC CAA ACA ACA GGT GCA AAT TCA GGT AAA
asn gly leu thr phe thr gln thr thr gly ala asn ser gly lys
                        2041/681
ACC GTC TAT GGC AAT GAT GGC TTG AAG TTT ACT AAT AGT GCT AAT
thr val tyr gly asn asp gly leu lys phe thr asn ser ala asn
2071/691                                  2101/701
AAA GCA CTT GGC GGC ACA ACT TAC ATC ACC AAA GAT CAA GTT GGT
lys ala leu gly gly thr thr tyr ile thr lys asp gln val gly
                        2131/711
TTT AGC AAT CAA GAT GGC TTA CTT GAT GAA AGC AAA CCG TAT CTT
phe ser asn gln asp gly leu leu asp glu ser lys pro tyr leu
2161/721                                  2191/731
AAC CGA GAA AAG CTA AAA GTT GGT AAA ATT GAG ATT AAA GAC AGT
asn arg glu lys leu lys val gly lys ile glu ile lys asp ser
                        2221/741
GGC ATT AAT GCA GGT GGT AAA GCC ATC ACA GGA CTG CCC TCA ACA
gly ile asn ala gly gly lys ala ile thr gly leu pro ser thr
2251/751                                  2281/761
CTG CCC AAC ACT ACC TAT ACT GCA CCT GGC GTG CAT ACT GCA CTA
leu pro asn thr thr tyr thr ala pro gly val his thr ala leu
                        2311/771
CAT GGC AGT ACA ATT TCT AAC GAC GAC AAA ACC CGT GCC GCC AGT
his gly ser thr ile ser asn asp asp lys thr arg ala ala ser
```

Fig 6 cont

```
2341/781                                    2371/791
ATC GCC GAT GTG CTA AAC GCA GGC TTT AAC TTG GAA GGT AAT GGT
ile ala asp val leu asn ala gly phe asn leu glu gly asn gly
                           2401/801
GAA GCG GTT GAC TTT GTC TCC ACT TAT GAC ACC GTC AAC TTT GCC
glu ala val asp phe val ser thr tyr asp thr val asn phe ala
2431/811                                    2461/821
GAT GGC AAT GCC ACC ACC GCT AAG GTA ACT TAT GAT AAC AAA ACC
asp gly asn ala thr thr ala lys val thr tyr asp asn lys thr
                           2491/831
AGT AAA GTG GCG TAT GAT GTC AAT GTG GAT GGT ACA ACC ATT CAT
ser lys val ala tyr asp val asn val asp gly thr thr ile his
2521/841                                    2551/851
CTA ACA GGC ACT AAT GGC AAG AAA AAC CAA ATT GGC GTA AAA ACC
leu thr gly thr asn gly lys lys asn gln ile gly val lys thr
                           2581/861
ACC ACA CTG ACC ACA AAA CGT GCT AAA GGT AAT ACA GCA ACT AAT
thr thr leu thr thr lys arg ala lys gly asn thr ala thr asn
2611/871                                    2641/881
TTT AGT GTT AAC TCT GGT GAT GAC AAT GCC CTT ATT AAC GCC AAA
phe ser val asn ser gly asp asp asn ala leu ile asn ala lys
                           2671/891
GAC ATC GCC GAC AAT CTA AAC ACC CTA GCT GGT GAA ATT CGC ACC
asp ile ala asp asn leu asn thr leu ala gly glu ile arg thr
2701/901                                    2731/911
GCC AAA GGC ACA GCA AGC ACC GCC CTA CAA ACC TTC TCT ATT ATT
ala lys gly thr ala ser thr ala leu gln thr phe ser ile ile
                           2761/921
GAT GAA CAA GGT AAT AAC TTT ATG GTC GGT AAC CTT TAC TCT GGT
asp glu gln gly asn asn phe met val gly asn leu tyr ser gly
2791/931                                    2821/941
TAT GAC ACC TCA AAT ACC TCT GAG ACC GTC ACC TTT GTA GGT GAA
tyr asp thr ser asn thr ser glu thr val thr phe val gly glu
                           2851/951
AAC GGC ATT ACC ACC AAG GTA AAT AAA GGT AAA GTC AAA GTT GGT
asn gly ile thr thr lys val asn lys gly lys val lys val gly
2881/961                                    2911/971
ATT GAC CAA ACC AAA GGC TTA ACC ACG CCT AAG CTG ACC GTG GGT
ile asp gln thr lys gly leu thr thr pro lys leu thr val gly
                           2941/981
AGT AGT AAT GGC AAA GGC ATT GTC ATT GAC AGT AAA GAT GGT CAA
ser ser asn gly lys gly ile val ile asp ser lys asp gly gln
```

Fig 6 cont

```
2971/991                                              3001/1001
AAT ACC ATC ACA GGA CTA AGC AAC ACT CTA ACC GAT GCC ACC AAC
asn thr ile thr gly leu ser asn thr leu thr asp ala thr asn
                              3031/1011
GCA ACA ACA GGG CAT GTC AGT GAA ATC CAG GGC TTG GCA CAA GGT
ala thr thr gly his val ser glu ile gln gly leu ala gln gly
3061/1021                                             3091/1031
GCA AAC AAA ACC CGT GCC GCC AGC ATT GGT GAT GTA CTA AAC GCA
ala asn lys thr arg ala ala ser ile gly asp val leu asn ala
                              3121/1041
GGC TTT AAC TTG CAA GGC AAT GGT GAA GCC AAA GAC TTT GTC TCC
gly phe asn leu gln gly asn gly glu ala lys asp phe val ser
3151/1051                                             3181/1061
ACT TAT GAC ACC GTC AAC TTT ATC GAT GGC AAT GCC ACC ACC GCT
thr tyr asp thr val asn phe ile asp gly asn ala thr thr ala
                              3211/1071
AAG GTG ACC TAT GAT GAC ACG AAA CAG ACC AGC ACA GTA ACT TAT
lys val thr tyr asp asp thr lys gln thr ser thr val thr tyr
3241/1081                                             3271/1091
GAT GTC AAT GTG GAT AAT AAA ACC CTT GAA GTG ACA GGC GAT AAA
asp val asn val asp asn lys thr leu glu val thr gly asp lys
                              3301/1101
AAA CTT GGC GTC AAA ACC ACC ACA CTG ACC AAA ACA AGT GCT AAT
lys leu gly val lys thr thr thr leu thr lys thr ser ala asn
3331/1111                                             3361/1121
GGT AAT GCA ACC AAA TTT AGT GCC GCC GAT GGC GAT GCC CTT GTT
gly asn ala thr lys phe ser ala ala asp gly asp ala leu val
                              3391/1131
AAA GCC AGT GAT ATC GCC ACC CAT CTA AAT ACC TTG GCT GGC GAC
lys ala ser asp ile ala thr his leu asn thr leu ala gly asp
3421/1141                                             3451/1151
ATC CAA ACC GCC AAA GGA GCA AGC CAA GCA AGC AGC TCA GCA AGC
ile gln thr ala lys gly ala ser gln ala ser ser ser ala ser
                              3481/1161
TAT GTG GAT GCT GAT GGC AAC AAG GTC ATC TAT GAC AGT ACC GAT
tyr val asp ala asp gly asn lys val ile tyr asp ser thr asp
```

Fig 6 cont

```
3511/1171                              3541/1181
AAG AAG TAC TAT CAA GCC AAA AAT GAT GGC ACA GTT GAT AAA ACC
lys lys tyr tyr gln ala lys asn asp gly thr val asp lys thr
                         3571/1191
AAA GAA GTT GCC AAA GAC AAA CTG GTC GCC CAA GCC CAA ACC CCA
lys glu val ala lys asp lys leu val ala gln ala gln thr pro
3601/1201                              3631/1211
GAT GGC ACA TTG GCT CGA ATG AAT GTC AAA TCA GTC ATT AAC AAA
asp gly thr leu ala arg met asn val lys ser val ile asn lys
                         3661/1221
GAA CAA GTA AAT GAT GCC AAT AAA AAG CAA GGC ATC AAC GAA GAC
glu gln val asn asp ala asn lys lys gln gly ile asn glu asp
3691/1231                              3721/1241
AAC GCC TTT GTT AAA GGA CTT GAA AAA GCC GCT TCT GAT AAC AAA
asn ala phe val lys gly leu glu lys ala ala ser asp asn lys
                         3751/1251
ACC AAA AAC GCC GCA GTA ACT GTG GGT GAT TTA AAT GCC GTT GCC
thr lys asn ala ala val thr val gly asp leu asn ala val ala
3781/1261                              3811/1271
CAA ACA CCG CTG ACC TTT GCA GGG GAT ACA GGC ACA ACG GCT AAA
gln thr pro leu thr phe ala gly asp thr gly thr thr ala lys
                         3841/1281
AAA CTG GGC GAG ACT TTG ACC ATC AAA GGT GGG CAA ACA GAC ACC
lys leu gly glu thr leu thr ile lys gly gly gln thr asp thr
3871/1291                              3901/1301
AAT AAG CTA ACC GAT AAT AAC ATC GGT GTG GTA GCA GGT ACT GAT
asn lys leu thr asp asn asn ile gly val val ala gly thr asp
                         3931/1311
GGC TTC ACT GTC AAA CTT GCC AAA GAC CTA ACC AAT CTT AAC AGC
gly phe thr val lys leu ala lys asp leu thr asn leu asn ser
3961/1321                              3991/1331
GTT AAT GCA GGT GGC ACC AAA ATT GAT GAC AAA GGC GTG TCT TTT
val asn ala gly gly thr lys ile asp asp lys gly val ser phe
                         4021/1341
GTA GAC GCA AAC GGT CAA GCC AAA GCA AAC ACC CCT GTG CTA AGT
val asp ala asn gly gln ala lys ala asn thr pro val leu ser
4051/1351                              4081/1361
GCC AAT GGG CTG GAC CTG GGT GGC AAA CGC ATC AGT AAC ATC GGT
ala asn gly leu asp leu gly gly lys arg ile ser asn ile gly
```

Fig 6 cont

```
                         4111/1371
GCA GCT GTT GAT GAT AAC GAT GCG GTG AAC TTT AAG CAG TTT AAT
ala ala val asp asp asn asp ala val asn phe lys gln phe asn
4141/1381                                   4171/1391
GAA GTT GCC AAA ACG GTC AAC AAC CTA AAC AAC CAA AGT AAC TCA
glu val ala lys thr val asn asn leu asn asn gln ser asn ser
                         4201/1401
GGT GCG TCA TTG CCC TTT GTA GTA ACC GAT GCC AAT GGC AAG CCC
gly ala ser leu pro phe val val thr asp ala asn gly lys pro
4231/1411                                   4261/1421
ATC AAT GGC ACC GAT GAC AAG CCC CAA AAA GCC ATC AAG GGC GCC
ile asn gly thr asp asp lys pro gln lys ala ile lys gly ala
                         4291/1431
GAT GGT AAA TAC TAT CAC GCC AAC GCC AAC GGC GTA CCT GTG GAC
asp gly lys tyr tyr his ala asn ala asn gly val pro val asp
4321/1441                                   4351/1451
AAA GAT GGC AAC CCC ATC ACC GAT GCG GAC AAA CTT GCC AAT CTG
lys asp gly asn pro ile thr asp ala asp lys leu ala asn leu
                         4381/1461
GCA GCT CAT GGC AAA CCC CTT GAT GCA GGT CAT CAA GTG GTG GCA
ala ala his gly lys pro leu asp ala gly his gln val val ala
4411/1471                                   4441/1481
AGC CTA GGC GGC AAC TCA GAT GCC ATC ACC CTA ACC AAC ATC AAG
ser leu gly gly asn ser asp ala ile thr leu thr asn ile lys
                         4471/1491
TCC ACT TTG CCA CAA ATT GAC ACA CCA AAC ACA GGT AAT GCC AAT
ser thr leu pro gln ile asp thr pro asn thr gly asn ala asn
4501/1501                                   4531/1511
GCA GGG CAA GCC CAA AGT CTG CCC AGC CTA TCA GCA GCA CAG CAA
ala gly gln ala gln ser leu pro ser leu ser ala ala gln gln
                         4561/1521
AGT AAT GCT GCC AGT GTC AAA GAT GTG CTA AAT GTA GGC TTT AAC
ser asn ala ala ser val lys asp val leu asn val gly phe asn
4591/1531                                   4621/1541
TTG CAG ACC AAT CAC AAT CAA GTG GAC TTT GTC AAA GCC TAT GAT
leu gln thr asn his asn gln val asp phe val lys ala tyr asp
                         4651/1551
ACC GTC AAC TTT GTC AAT GGT ACA GGT GCC GAC ATC ACA AGC GTG
thr val asn phe val asn gly thr gly ala asp ile thr ser val
```

Fig 6 cont

```
4681/1561                                    4711/1571
CGT AGT GCT GAT GGC ACG ATG AGT AAC ATC ACC GTC AAC ACC GCC
arg ser ala asp gly thr met ser asn ile thr val asn thr ala
                                4741/1581
TTA GCA GCG ACC GAT GAT GAT GGC AAT GTG CTT ATC AAA GCC AAA
leu ala ala thr asp asp asp gly asn val leu ile lys ala lys
4771/1591                                    4801/1601
GAT GGT AAG TTC TAC AAA GCA GAC GAC CTC ATG CCA AAC GGC TCA
asp gly lys phe tyr lys ala asp asp leu met pro asn gly ser
                                4831/1611
CTA AAA GCA GGC AAA TCA GCC AGT GAT GCC AAA ACT CCA ACT GGT
leu lys ala gly lys ser ala ser asp ala lys thr pro thr gly
4861/1621                                    4891/1631
CTA AGC CTT GTC AAC CCC AAT GCT GGT AAA GGC AGT ACA GGC GAT
leu ser leu val asn pro asn ala gly lys gly ser thr gly asp
                                4921/1641
GCA GTG GCT CTT AAT AAC TTA TCA AAA GCG GTA TTT AAA TCC AAA
ala val ala leu asn asn leu ser lys ala val phe lys ser lys
4951/1651                                    4981/1661
GAT GGT ACA ACT ACT ACC ACA GTA AGC TCT GAT GGC ATC AGT ATC
asp gly thr thr thr thr thr val ser ser asp gly ile ser ile
                                5011/1671
CAA GGC AAA GAT AAC AGC AAC ATC ACC CTA AGC AAA GAT GGG CTG
gln gly lys asp asn ser asn ile thr leu ser lys asp gly leu
5041/1681                                    5071/1691
AAT GTA GGC GGT AAG GTC ATC AGC AAT GTG GGT AAA GGC ACA AAA
asn val gly gly lys val ile ser asn val gly lys gly thr lys
                                5101/1701
GAC ACC GAC GCT GCC AAT GTA CAA CAG TTA AAC CGA AGT ACG CAA
asp thr asp ala ala asn val gln gln leu asn arg ser thr gln
5131/1711                                    5161/1721
CTT GTT GGG TCT TGG GTA ATG GCT GGT AAT GAT AAC GCT GAC GGC
leu val gly ser trp val met ala gly asn asp asn ala asp gly
                                5191/1731
AAT CAG GTA AAC ATT GCC GAC ATC AAA AAA GAC CCA AAT TCA GGT
asn gln val asn ile ala asp ile lys lys asp pro asn ser gly
5221/1741                                    5251/1751
TCA TCA TCT AAC CGC ACT GTC ATC AAA GCA GGC ACG GTA CTT GGC
ser ser ser asn arg thr val ile lys ala gly thr val leu gly
                                5281/1761
GGT AAA GGT AAT AAC GAT ACC GAA AAA CTT GCC ACT GGT GGT GTA
gly lys gly asn asn asp thr glu lys leu ala thr gly gly val
```

Fig 6 cont

```
5311/1771                              5341/1781
CAA GTG GGC GTG GAT AAA GAC GGC AAC GCT AAC GGC GAT TTA AGC
gln val gly val asp lys asp gly asn ala asn gly asp leu ser
                        5371/1791
AAT GTT TGG GTC AAA ACC CAA AAA GAT GGC AGC AAA AAA GCC CTG
asn val trp val lys thr gln lys asp gly ser lys lys ala leu
5401/1801                              5431/1811
CTC GCC ACT TAT AAC GCC GCA GGT CAG ACC AAC TAT TTG ACC AAC
leu ala thr tyr asn ala ala gly gln thr asn tyr leu thr asn
                        5461/1821
AAC CCC GCA GAA GCC ATT GAC AGA ATA AAT GAA CAA GGT ATC CGC
asn pro ala glu ala ile asp arg ile asn glu gln gly ile arg
5491/1831                              5521/1841
TTC TTC CAT GTC AAC GAT GGC AAT CAA GAG CCT GTG GTA CAA GGG
phe phe his val asn asp gly asn gln glu pro val val gln gly
                        5551/1851
CGT AAC GGC ATT GAC TCA AGT GCC TCA GGC AAG CAC TCA GTG GCG
arg asn gly ile asp ser ser ala ser gly lys his ser val ala
5581/1861                              5611/1871
GTC GGT TAT AAG GCC AAG GCA GAT GGT GAA GCC GCC GTT GCC ATA
val gly tyr lys ala lys ala asp gly glu ala ala val ala ile
                        5641/1881
GGC AGA CAA ACC CAA GCA GGC AAC CAA TCC ATC GCC ATC GGT GAT
gly arg gln thr gln ala gly asn gln ser ile ala ile gly asp
5671/1891                              5701/1901
AAC GCA CAA GCC ACA GGC GAT CAA TCC ATC GCC ATC GGT ACA GGC
asn ala gln ala thr gly asp gln ser ile ala ile gly thr gly
                        5731/1911
AAT GTG GTA GCA GGT AAG CAC TCT GGT GCC ATC GGC GAC CCA AGC
asn val val ala gly lys his ser gly ala ile gly asp pro ser
5761/1921                              5791/1931
ACT GTT AAG GCT GAT AAC AGT TAC AGT GTG GGT AAT AAC AAC CAG
thr val lys ala asp asn ser tyr ser val gly asn asn asn gln
                        5821/1941
TTT ACC GAT GCC ACT CAG ACC GAT GTC TTT GGT GTG GGC AAT AAC
phe thr asp ala thr gln thr asp val phe gly val gly asn asn
5851/1951                              5881/1961
ATC ACC GTG ACC GAA AGT AAC TCG GTT GCC TTA GGT TCA AAC TCT
ile thr val thr glu ser asn ser val ala leu gly ser asn ser
```

Fig 6 cont

```
                              5911/1971
GCC ATC AGT GCA GGC ACA CAC GCA GGC ACA CAA GCC AAA AAA TCT
ala ile ser ala gly thr his ala gly thr gln ala lys lys ser
5941/1981                                       5971/1991
GAC GGC ACA GCA GGT ACA ACC ACC ACA GCA GGT GCA ACA GGT ACG
asp gly thr ala gly thr thr thr thr ala gly ala thr gly thr
                              6001/2001
GTT AAA GGC TTT GCT GGA CAA ACG GCG GTT GGT GCG GTC TCC GTG
val lys gly phe ala gly gln thr ala val gly ala val ser val
6031/2011                                       6061/2021
GGT GCC TCA GGT GCT GAA CGC CGT ATC CAA AAT GTG GCA GCA GGT
gly ala ser gly ala glu arg arg ile gln asn val ala ala gly
                              6091/2031
GAG GTC AGT GCC ACC AGC ACC GAT GCG GTC AAT GGT AGC CAG TTG
glu val ser ala thr ser thr asp ala val asn gly ser gln leu
6121/2041                                       6151/2051
TAC AAA GCC ACC CAA AGC ATT GCC AAC GCA ACC AAT GAG CTT GAC
tyr lys ala thr gln ser ile ala asn ala thr asn glu leu asp
                              6181/2061
CAT CGT ATC CAC CAA AAC GAA AAT AAA GCC AAT GCA GGG ATT TCA
his arg ile his gln asn glu asn lys ala asn ala gly ile ser
6211/2071                                       6241/2081
TCA GCG ATG GCG ATG GCG TCC ATG CCA CAA GCC TAC ATT CCT GGC
ser ala met ala met ala ser met pro gln ala tyr ile pro gly
                              6271/2091
AGA TCC ATG GTT ACC GGG GGT ATT GCC ACC CAC AAC GGT CAA GGT
arg ser met val thr gly gly ile ala thr his asn gly gln gly
6301/2101                                       6331/2111
GCG GTG GCA GTG GGA CTG TCG AAG CTG TCG GAT AAT GGT CAA TGG
ala val ala val gly leu ser lys leu ser asp asn gly gln trp
                              6361/2121
GTA TTT AAA ATC AAT GGT TCA GCC GAT ACC CAA GGC CAT GTA GGG
val phe lys ile asn gly ser ala asp thr gln gly his val gly
6391/2131
GCA GCA GTT GGT GCA GGT TTT CAC TTT TAA GCCATAAATCGC
ala ala val gly ala gly phe his phe stop

AGATTTTACTTAAAAATCAATCTCACCATAGTTGTATAAAACAGCATCA inverted repeat                                 6505
GCATCAGTCATATTACTGATGCTTGATGGTTTTTATTACTTAAACCATTTTA
```

| | Bc5 | BBH17 | Perez112 | RH1 | RH4 | ATCC 25238; UspA1 | ATCC 25238; UspA2 |
|---|---|---|---|---|---|---|---|
| Bc5 | 100 % / 100 % | | | | | | |
| BBH17 | 83.5 % / 88.1 % | 100 % / 100 % | | | | | |
| Perez112 | 79.2 % / 82.6 % | 78.3 % / 81.4 % | 100 % / 100 % | | | | |
| RH1 | 75.8 % / 80.2 % | 76.3 % / 79.6 % | 85.0 % / 89.1 % | 100 % / 100 % | | | |
| RH4 | 65.6 % / 71.3 % | 65.3 % / 71.2 % | 68.0 % / 72.9 % | 67.7 % / 71.7 % | 100 % / 100 % | | |
| ATCC 25238; UspA1 | 11.1 % / 17.9 % | 9.5 % / 14.9 % | 11.1 % / 17.5 % | 5.5 % / 8.3 % | 10.0 % / 15.6 % | 100 % / 100 % | |
| ATCC 25238; UspA2 | 6.7 % / 12.1 % | 6.7 % / 11.1 % | 7.5 % / 12.4 % | 7.3 % / 12.4 % | 6.5 % / 11.1 % | 28.8 % / 38.3 % | 100 % / 100 % |

MID-1 (Bc5) protein(top), patent US 5808024(bottom)

```
         10        20        30        40        50        60        70        80
          |         |         |         |         |         |         |         |
MNHIYKVIFNKATGTFMAVAEYAKSHSTGGSCATGQVGSVCTLSFARVAALAVLVIGATLNGSAYAQQDPRHIAIDGNSSNT 90       100       110       120       130       140       150       160
          |         |         |         |         |         |         |         |
SSGTARATGDRAIALGENANAEGGQAIAIGSSNKTGGRNALNIGTDAKGEESIAIGGDVVAEGTASIAIGGDDLHLWDEPNK 170       180       190       200       210       220       230       240
          |         |         |         |         |         |         |         |
QKFLDPKVKELILKHQELNNIYKLPDGSPQRYFRTYAKGHASIALGTMTQAEGHFANAFGTRATAKGNYSLAVGLTAQANTE
                                     . ...  ............  ........ ..
                                     MSYAQGHFSNAFGTRATAKSAYSLAVGLAATAEGQ
                                              |         |         |
                                              10        20        30

250       260       270       280       290       300       310       320
          |         |         |         |         |         |         |         |
SSIAVGSNAQANGFAATAIGGGTKADLGRSIALGFGSQILTKEKDSHNNTNVYVPQGEILEERYKATENGQSPNKVVDIFSI
 . ....   . .... ..    .....   ..                  .                .. .
STIAIGSDATSSSLGAIALGAGTRAQLQGSIALGQGSVVTQSDNNSRPAYTPNTQALDPKFQATNNTKAGPLSIGSN-----
 |         |         |         |         |         |         |         |
 40        50        60        70        80        90       100       110

330       340       350       360       370       380       390       400
          |         |         |         |         |         |         |         |
GSSSIKRKIINVGAGSQETDAVNVAQLKLVERVAKRQ-ITFQGDDSNNSVKKGLGQTLTIKGGKTETGELTENNIGVVQDDN
   ............  .........-  . ..   ........    .. ..  ........
---SIKRKIINVGAGVNKTDAVNVAQLEAVVKWAKERRITFQGDDNSTDVKIGLDNTLTIKGGAETNA--------------
    |         |         |         |         |         |
    120       130       140       150       160       170

410       420       430       440       450       460       470       480       490
          |         |         |         |         |         |         |         |         |
GNGLKVKLAKDLTGLTKVAVNGNGANNAELLNGGLTFSTSGANAGKTVYGTDGVKFTNNTGTGTGTAIPDTTRITKNKIGFA
-------------------------------------------------------------------------------

500       510       520       530       540       550       560       570
          |         |         |         |         |         |         |         |
GADEQVDESKPYLDNEKLKVGTVEIKKTGINAGNQEITKVKSAIVDAVNGQANQSFVNLLETAGTNTNKQNSAATVKDLYDL
--------------------------------------------------------------------------------
```

Fig 8

```
           580       590       600       610       620       630       640       650
            |         |         |         |         |         |         |         |
SQSPLTFTGDSGNVKRKLGQTLTITGGQTKTDQLTDNNIGVVAGTNGLT--VKLAKTLNSLTEVNTATLNATNKVKVDNSTG
                                    .........      .........  ......  .....  ...  .
------------------------------------LTDNNIGVVKEADNSGLKVKLAKTLNNLTEVNTTTLNATTTVKVGSSSS
                                    |         |         |         |         |
                                   180       190       200       210       220

660       670       680       690       700       710       720       730
            |         |         |         |         |         |         |         |
NTAELLNNGLTFTQTTGANSGKTVYGNDGLKFTNSANKALGGTTYITKDQVGFSNQDGLLDESKPYLNREKLKVGKIEIKDS
 .....     .....                  .           .         .           .  .
TTAELLSDSLTFTQPNTGSQSTSKTVYGVNGVKFTNNAETTAAIGTTRITRDKIGFARDGDVDEKQAPYLDKKQLKVGSVAI
 |         |         |         |         |         |         |         |
230       240       250       260       270       280       290       300

---------------------------------------------------------------------------------
TIDNGIDAGNKKISNLAKGSSANDAVTIEQLKAAKPTLNAGAGISVTPTEISVDAKSGNVTAPTYNIGVKTTELNSDGTSDK
 |         |         |         |         |         |         |         |         |
310       320       330       340       350       360       370       380       390

---------------------------------------------------------------------------------
FSVKGSGTNNNSLVTAEHLASYLNEVNRTADSALQSFTVKEEDDDDANAITVAKDTTKNAGAVSILKLKGKNGLTVATKKDGT
 |         |         |         |         |         |         |         |
400       410       420       430       440       450       460       470

VTFGLSQDSGLTIGKSTLNNDGLTVKDTNEQIQVGANGIKFTNVNGSNPGTGIANTARITRDKIGFAGSDGAVDTNKPYLDQ
 |         |         |         |         |         |         |         |
480       490       500       510       520       530       540       550

740       750       760       770
                  |         |         |         |
-----------GINAGGKAITGLPSTLPNTTYTAPGVHTALHGSTISND---------------------------------
            ............   ...
DKLQVGNVKITNTGINAGGKAITGLSPTLPSIADQSSRNIELGNTIQDKDKSNAASINDILNTGFNLKNNNNPIDFVSTYDI
 |         |         |         |         |         |         |         |
560       570       580       590       600       610       620       630

---------------------------------------------------------------------------------
VDFANGNATTATVTHDTANKTSKVVYDVNVDDTTIHLTGTDDNKKLGVKTTKLNKTSANGNTATNFNVNSSDEDALVNAKDI
 |         |         |         |         |         |         |
640       650       660       670       680       690       700       710
```

```
AENLNTLAKEIHTTKGTADTALQTFTVKKVDENNNADDANAITVGQKNANNQVNTLTLKGENGLNIKTDKNGTVTFGINTTS
    |        |        |        |        |        |        |        |        |
   720      730      740      750      760      770      780      790      800
```

```
GLKAGKSTLNDGGLSIKNPTGSEQIQVGADGVKFAKVNNNGVVGAGIDGTTRITRDEIGFTGTNGSLDKSKPHLSKDGINAG
    |        |        |        |        |        |        |        |        |
   810      820      830      840      850      860      870      880
```

```
GKKITNIQSGEIAQNSHDAVTGGKIYDLKTELENKISSTAKTAQNSLHEFSVADEQGNNFTVSNPYSSYDTSKTSDVITFAG
    |        |        |        |        |        |        |        |
   890      900      910      920      930      940      950      960
```

```
                                                                         -DKTR
                                                                          ....
ENGITTKVNKGVVRVGIDQTKGLTTPKLTVGNNNGKGIVIDSQNGQNTITGLSNTLANVTNDKGSVRTTEQGNIIKDEDKTR
    |        |        |        |        |        |        |        |
   970      980      990     1000     1010     1020     1030     1040
```

```
   780      790      800      810      820      830      840      850
    |        |        |        |        |        |        |        |
AASIADVLNAGFNLEGNGEAVDFVSTYDTVNFADGNATTAKVTYDNKTSKV--AYDVNVDGTTIHLTGINGKKNQIGVKTTT
 ....   ...  ........................               ......  ...
AASIVDVLSAGFNLQGNGEAVDFVSTYDTVNFADGNATTAKVTYDDTSKTSKVVYDVNVDDTTIEVK--------------
    |        |        |        |        |        |        |
   1050     1060     1070     1080     1090     1100     1110
```

```
   860      870      880      890      900      910      920      930
    |        |        |        |        |        |        |        |
LTTKRAKGNTATNFSVNSGDDNALINAKDIADNLNTLAGEIRTAKGTASTALQTFSIIDEQGNNFMVGNLYSGYDTSNTSET
```

```
   940      950      960      970      980      990     1000     1010     1020
    |        |        |        |        |        |        |        |        |
VTFVGENGITTKVNKGKVKVGIDQTKGLTTPKLTVGSSNGKGIVIDSKDGQNTITGLSNTLTDATNATTGHVSEIQGLAQGA
```

```
NKTRAASIGDVLNAGFNLQGNGEAKDFVSTYDTVNFIDGNATTAKVTYDDTKQTSTVTYDVNVDNKTLEVTGDKKLGVKTTT
..............                                                      ..........
--------------------------------------------------------------------DKKLGVKTTT
                                                                    |
                                                                    1120

1110      1120      1130      1140      1150      1160      1170      1180
         |         |         |         |         |         |         |         |
LTKTSANGNATKFSAAD-GDALVKASDIATHLNTLAGDIQTAKGASQASSSASYVDADGNKVIYDSTDKKYYQAKNDGTVDK
 ..  .    .   .  ...........  .....  ............. ..  ...................  ....
LTSTGTGANKFALSNQATGDALVKASDIVAHLNTLSGDIQTAKGASQANNSAGYVDADGNKVIYDSTDNKYYQAKNDGTVDK
   |         |         |         |         |         |         |         |
   1130      1140      1150      1160      1170      1180      1190      1200

1190      1200      1210      1220      1230      1240      1250      1260
         |         |         |         |         |         |         |         |
TKEVAKDKLVAQAQTPDGTLARMNVKSVINKEQVNDANKKQGINEDNAFVKGLEKAASDNKTKNAAVTVGDLNAVAQTPLTF
.....................  ........................................................
TKEVAKDKLVAQAQTPDGTLAQMNVKSVINKEQVNDANKKQGINEDNAFVKGLEKAASDNKTKNAAVTVGDLNAVAQTPLTF
   |         |         |         |         |         |         |         |
   1210      1220      1230      1240      1250      1260      1270      1280

1270      1280      1290      1300      1310      1320      1330      1340
         |         |         |         |         |         |         |         |
AGDTGTTAKKLGETLTIKGGQTDTNKLTDNNIGVVAGTDGFTVKLAKDLTNLNSVNAGGTKIDDKGVSFVDANGQAKANTPV
...............................................................   ........
AGDTGTTAKKLGETLTIKGGQTDTNKLTDNNIGVVAGTDGFTVKLAKDLTNLNSVNAGGTKIDDKGVSFVDSSGQAKANTPV
   |         |         |         |         |         |         |         |
   1290      1300      1310      1320      1330      1340      1350      1360

1350      1360      1370      1380      1390      1400      1410      1420      1430
         |         |         |         |         |         |         |         |         |
LSANGLDLGGKRISNIGAAVDDNDAVNFKQFNEVAKTVNNLNNQSNSGASLPFVVTDANGKPINGTDDKPQKAIKGADGKYY
........
LSANGLDL------------------------------------------------------------------------
   |
   1370

1440      1450      1460      1470      1480      1490      1500      1510
         |         |         |         |         |         |         |         |
HANANGVPVDKDGNPITDADKLANLAAHGKPLDAGHQVVASLGGNSDAITLTNIKSTLPQIDTPNTGNANAGQAQSLPSLSA

--------------------------------------------------------------------------------

1520      1530      1540      1550      1560      1570      1580      1590
         |         |         |         |         |         |         |         |
AQQSNAASVKDVLNVGFNLQTNHNQVDFVKAYDTVNFVNGTGADITSVRSADGTMSNITVNTALAATDDDGNVLIKAKDGKF

--------------------------------------------------------------------------------

1600      1610      1620      1630      1640      1650      1660      1670
         |         |         |         |         |         |         |         |
```

YKADDLMPNGSLKAGKSASDAKTPTGLSLVNPNAGKGSTGDAVALNNLSKAVFKSKDGTTTTTVSSDGISIQKKINSKKVES
----------------------------------------------------------------------------------

```
          1680      1690      1700      1710      1720      1730      1740      1750
            |         |         |         |         |         |         |         |
KDGLNVGGKVISNVGKGTKDTDAANVQQLNRSTQLVGSWVMAGNDNADGNQVNIADIKKDPNSGSSSNRTVIKAGTVLGGKG
           ..  ..               ...........  .  .............................
------GGKVISNVGKGTKDTDAANVQQLNEVRNLLGLGN-AGNDNADGNQVNIADIKKDPNSGSSSNRTVIKAGTVLGGKG
            |         |         |         |         |         |         |         |
          1380      1390      1400      1410      1420      1430      1440      1450

1760      1770      1780      1790      1800      1810      1820      1830      1840
            |         |         |         |         |         |         |         |         |
NNDTEKLATGGVQVGVDKDGNANGDLSNVWVKTQKDGSKKALLATYNAAGQTNYLTNNPAEAIDRINEQGIRFFHVNDGNQE
..........    ...................................................................
NNDTEKLATGGIQVGVDKDGNANGDLSNVWVKTQKDGSKKALLATYNAAGQTNYLTNNPAEAIDRINEQGIRFFHVNDGNQE
            |         |         |         |         |         |         |         |         |
          1460      1470      1480      1490      1500      1510      1520      1530

1850      1860      1870      1880      1890      1900      1910      1920
            |         |         |         |         |         |         |         |
PVVQGRNGIDSSASGKHSVAVGYKAKADGEAAVAIGRQTQAGNQSIAIGDNAQATGDQSIAIGTGNVVAGKHSGAIGDPSTV
..............  .  ...............................................................
PVVQGRNGIDSSASGKHSVAIGFQAKADGEAAVAIGRQTQAGNQSIAIGDNAQATGDQSIAIGTGNVVAGKHSGAIGDPSTV
            |         |         |         |         |         |         |         |
          1540      1550      1560      1570      1580      1590      1600      1610

1930      1940      1950      1960      1970      1980      1990      2000
            |         |         |         |         |         |         |         |
KADNSYSVGNNNQFTDATQTDVFGVGNNITVTESNSVALGSNSAISAGTHAGTQAKKSDGTAGTTTTAGATGTVKGFAGQTA
..................................................................................
KADNSYSVGNNNQFTDATQTDVFGVGNNITVTESNSVALGSNSAISAGTHAGTQAKKSDGTAGTTTTAGATGTVKGFAGQTA
            |         |         |         |         |         |         |         |
          1620      1630      1640      1650      1660      1670      1680      1690

2010      2020      2030      2040      2050      2060      2070      2080
            |         |         |         |         |         |         |         |
VGAVSVGASGAERRIQNVAAGEVSATSTDAVNGSQLYKATQSIANATNELDHRIHQNENKANAGISSAMAMASMPQAYIPGR
..................................................................................
VGAVSVGASGAERRIQNVAAGEVSATSTDAVNGSQLYKATQSIANATNELDHRIHQNENKANAGISSAMAMASMPQAYIPGR
            |         |         |         |         |         |         |         |
          1700      1710      1720      1730      1740      1750      1760      1770      1780

2090      2100      2110      2120      2130
            |         |         |         |         |
SMVTGGIATHNGQGAVAVGLSKLSDNGQWVFKINGSADTQGHVGAAVGAGFHF
.....................................................
SMVTGGIATHNGQGAVAVGLSKLSDNGQWVFKINGSADTQGHVGAAVGAGFHF                Fig 8 cont
            |         |         |         |         |
          1790      1800      1810      1820      1830
```

SURFACE EXPLOSED IMMUNOGLOBULIN D-BINDING PROTEIN FROM MORAXELLA CATARRHALIS

FIELD OF THE INVENTION

The present invention relates to a surface exposed protein, which can be detected in *Moraxella catarrhalis*, having an amino acid sequence as described in SEQ ID NO 1, an apparent molecular weight of 200 kDa and a capacity of selectively binding membrane bound or soluble IgD, and to an immunogenic or IgD-binding fragment of said surface exposed protein, and to an immunogenic and adhesive fragment of said surface exposed protein.

BACKGROUND OF THE INVENTION

*Moraxella catarrhalis* is a Gram-negative diplococcus that for a long time was considered a relatively harmless commensal in the respiratory tract. At present, it is the third most frequent cause of otitis media and also a significant agent in sinusitis and lower respiratory tract infections in adults with pulmonary disease. *M. catarrhalis* is also one of the most common inhabitants of the pharynx of healthy children.

Two decades ago, *Haemophilus influenzae* and *M. catarrhalis* were shown to display a strong affinity for both soluble and surface-bound human IgD (1). The IgD-binding seems to be paralleled by a similar interaction with surface-bound IgD at the cellular level, a phenomenon that explains the strong mitogenic effects on human lymphocytes by *H. influenzae* and *M. catarrhalis* (2-4). An IgD-binding outer membrane protein from *H. influenzae* (protein D) was isolated and cloned, and shown to be an important pathogenicity factor (5). However, protein D does not bind to the majority of IgD myelomas tested, and it was suggested that encapsulated *H. influenzae* of serotype b expresses an additional IgD receptor (6).

Early studies demonstrated that the outer membrane proteins (OMPs) from a diverse collection of *Moraxella* isolates exhibit a high degree of similarity (7). Investigators have primarily focused their research efforts on a selected group of proteins. Recent studies have demonstrated that the high-molecular-weight surface antigen, termed UspA or HMW-OMP, is actually comprised of two different proteins. These proteins are named UspA1 and UspA2 (8,9,10). The apparent molecular masses of these OMPs are greater than 250 kDa as determined by SDS-PAGE analysis. Reduction with formic acid yields bands of approximately 120 to 140 kDa, suggesting that the UspA proteins form an oligomeric complex composed of several monomeric subunits (11). The predicted mass of each protein, as deduced from the cloned genes, is 88 kDa and 62 kDa for UspA1 and UspA2, respectively. It is thought that the difference in the deduced mass and the mass determined using SDS-PAGE is due to a predicted coiled coil structure (9).

In a recent patent publication, an outer membrane protein of *M. catarrhalis* with a molecular mass of approximately 200 kDa was isolated (12). A sequence encoding a protein of approximately 200 kDa was also provided. The protein was shown to be immunogenic, but no further biological functions were presented. In addition, a 200 kDa protein is associated with hemagglutinating *M. catarrhalis* (13,14).

CopB is an 80 kDa surface exposed major OMP that shows a moderate antigenic conservation. In addition, OMP CD is a 46 kDa highly conserved protein with numerous surface exposed epitopes and OMP E a 47 kDa protein detected on a variety of heterologous strains. The lactoferrin-binding (LbpA and B) and transferrin-binding (TbpA and B) proteins have molecular sizes of 99-111 and 74-105 kDa, respectively.

Certain strains of *Staphylococcus aureus* produce immunostimulatory exotoxins such as toxic shock syndrome toxin-1 (TSST-1), staphylococcal enterotoxin A (SEA), SEB and SEC, all of which are associated with food poisoning and toxic shock syndrome (TSS). These exotoxins have been denominated as superantigens (SAg) due to their ability to activate a high frequency of T lymphocytes. SAg bind as unprocessed proteins to HLA class II molecules on APC and oligoclonally activate T cells expressing particular TCR VD chains. In vivo exposure to excessive amounts of SAg results in a strong cytokine production and includes IL-2, TNF-α and IFN-γ, which are associated with a toxic shock like syndrome.

Since the discovery of the first immunoglobulin-binding bacterial protein, *S. aureus* protein A (SpA) in 1966, this protein has been extensively characterized. The ability of SpA to bind the Fc part of IgG is well known, but SpA also binds a fraction of Ig-molecules of all classes due to the so called 'alternative' binding, which represents an interaction with the variable region of certain heavy chains. All IgG-binding capacity of *S. aureus* has been considered to be mediated by SpA. However, the existence of a second gene in *S. aureus* encoding an Ig-binding protein has also been reported.

*Streptococcus pyogenes* and *Peptostreptococcus magnus* are other examples of Ig-binding bacteria. *S. pyogenes* produces protein H belonging to the M family of proteins, and has strong affinity for the Fc region of IgG. Proteins expressed by some strains bind IgA instead of IgG or both IgG and IgA. Protein Bac or the B-antigen is an IgA-binding protein expressed by certain strains of group B streptococci. Finally, *P. magnus* expresses protein L that shows high and specific affinity for Ig light chains, especially k light chains, and thereby interacts with all classes of Ig.

IgD is a unique immunoglobulin that exists in both a soluble and a surface-bound form. Both forms are encoded by the same gene and are splicing products. All mature B lymphocytes have B cell receptors (BCR) consisting of membrane-bound IgD and IgM. Soluble IgD comprises approximtely 0.25% of the total amount of serum-Ig. The main function of IgD seems to be as an antigen-receptor on the B cell surface in order to optimize B cell recruitment and accelerated affinity maturation. Antigen is taken up through IgD by endocytosis followed by intracellular degradation and presentation on MHC class II for T cells, which in turn are activated and produce cytokines. Hereby, T cell help is obtained including numerous cytokines (e.g. interleukin-4) and co-stimulatory molecules such as CD28.

Despite macrophages, dendritic cells, and B cells all can present antigens to T lymphocytes, the B cells are 100-fold more efficient due to the importance of the antigen-presenting immunoglobulin on the surface. An attractive strategy in order to potentiate immunization is to directly target an antigen to the B cell receptor. It was early shown that the mouse antibody-response against bovine serum albumin (BSA) conjugated to anti-IgD monoclonal antibodies was 100-fold stronger compared to BSA administration without any antibody. In paralell, it has been demonstrated that a mouse myeloma antigen incorporated into the constant region of anti-IgD-antibodies targeted to the surface-bound IgD results in an up to 1000-fold more efficient antigen presentation on MHC class II (15).

Tolerance induction can be achieved experimentally by B cell activation through the IgD BCR without any additional T cell help. It would also be possible to treat autoimmune diseases by inducing B cell anergy and thus inhibit the production of auto-antibodies. In fact, SLE-prone mice administered dextran-conjugated anti-IgD antibodies exhibit a delayed development of autoimmunity. In yet another study it was shown that B cell activation via IgD decreases a T helper 2-induced IgE response suggesting a therapy for diminishing the IgE production in severely allergic individuals by displacing the antibody response from a Th2- to a Th1-response. By targeting antigens to the B cell receptor IgD, stimulation, tolerance, and a switch from IgE-production can be achieved. In addition, polyclonal activation has been reported. The outcome is depending on the experimental model used. With different constructs including various repeating IgD-binding segments, it is possible to tailor the response.

The T cell is a significant player in the anti-tumour response since it recognizes tumour-specific antigens. However, the important T cells display commonly depressed activity in the cancer patient due to a general immunosuppression. A triggering of T helper cells would therefore be very beneficial. Vaccination against tumours using antigen presenting cells (APC) has recently been acknowledged (17). Immunization protocols with APC pulsed ex vivo with tumor antigens (peptides) have been shown to induce effective MHC class I presentation for cytotoxic T cells. It has also been demonstrated that EBV-transformed B cells are able to present melanoma antigens for tumour-infiltrating lymphocytes (TIL). In experimental models, it has also been shown that tumour cells transfected with MHC class II and B7 surface molecules, receptors that are aboundant on B cells, would be a feasible approach for tumour vaccination. Interestingly, B16 melanoma bearing mice that were injected with B cells pulsed with a tumour lysate from the corresponding cell line showed a prolonged survival due to an increase in IFN-γ producing T cells. It was also demonstrated that the induced T helper cells evoked a stronger cytotoxic response against the solid tumours. Since myeloma antigen targeted to IgD induces a T cell response, the suggested approach using IgD-binding bacterial proteins conjugated to specific tumour antigens would be feasible.

To target an antigen (e.g. peptide derived from a microbe or a specific tumour) to IgD-bearing B cells in order to trigger both humoral and cellular immune responses a IgD-binding protein or a shorter IgD-binding peptide would be a very feasible vector. Several examples of successful strategies with a similar angle of approach exist. The humoral immune response in mice against bovine serum albumin (BSA) conjugated to anti-IgD monoclonal antibodies is 100-fold stronger compared to when BSA is administered alone. A recent publication by Lunde et al. (15) describes that when a myeloma-derived peptide is integrated in the constant region of anti-IgD Fab' fragments and injected into mice, a 1,000-fold more efficient antigen presentation is achieved against the antigen in question (15). In parallel, the Ig-binding fragment of *S. aureus* protein A fused with cholera toxin significantly increases both systemic and mucosal immune responses 10- to 100-fold against the cholera toxin (16). Finally, in a mouse tumour model consisting of the experimentally well defined B16 melanoma, activated B lymphocytes that are pulsed ex vivo with peptides derived from the tumour tissue can evoke a stronger anti-tumour response in vivo and consequently a prolonged survival (17).

SUMMARY OF THE INVENTION

In one aspect the present invention relates to a surface exposed protein, which can be detected in *Moraxella catarrhalis*, having an amino acid sequence as described in SEQ ID NO 1, an apparent molecular weight of 200 kDa and a capacity of selectively binding membrane bound or soluble IgD, or naturally occurring or artificially modified variants thereof, or an immunogenic or IgD-binding fragment of said protein or variants, or an immunogenic and adhesive fragment of said surface exposed protein.

In another aspect the present invention relates to an immunogenic or IgD-binding fragment of a surface exposed protein as defined above, which fragment can be detected in *Moraxella catarrhalis*, having a capacity of selectively binding membrane bound or soluble IgD, or naturally occurring or artificially modified variants thereof.

In a further aspect the present invention relates to an immunogenic or IgD-binding fragment as described above, having an amino acid sequence as described in SEQ ID NO 10.

In still a further aspect the present invention relates to an immunogenic and adhesive fragment of a surface exposed protein as defined above, which fragment can be detected in *Moraxella catarrhalis*, having a capacity of binding erythrocytes and epithelial cells.

In still another aspect the present invention relates to an immunogenic and adhesive fragment as defined above, having an amino acid sequence as described in SEQ ID NO 8.

In one aspect the present invention relates to a DNA segment comprising a DNA sequence, as shown in SEQ ID NO 2, which DNA sequence codes for a surface exposed protein of *Moraxella catarrhalis* as defined above, or naturally occurring or artificially modified variants of said DNA sequence.

In yet another aspect the present invention relates to a DNA segment comprising a DNA sequence which codes for an immunogenic or IgD-binding fragment as defined above.

In a further aspect the present invention relates to a DNA segment as defined above, comprising a DNA sequence, as shown in SEQ ID NO 11, which DNA sequence codes for an immunogenic or IgD-binding fragment as defined above.

In still a further aspect the present invention relates to a DNA segment comprising a DNA sequence, which codes for an immunogenic and adhesive fragment of a surface exposed protein as defined above.

In another aspect the present invention relates to a DNA segment as above, comprising a DNA sequence, as shown in SEQ ID NO 9, which DNA sequence codes for an immunogenic and adhesive fragment as defined above.

In a further aspect the present invention relates to a vaccine containing a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants of said protein, or an immunogenic or IgD-binding fragment of said protein or variants, or an immunogenic and adhesive fragment of said surface exposed protein.

In another aspect the present invention relates to a vaccine containing an immunogenic or IgD-binding fragment of a surface exposed protein of *Moraxella catarrhalis*, which has a capacity of selectively binding membrane bound or soluble IgD, or naturally occurring or artificially modified variants of said fragment, preferably a vaccine containing an immunogenic or IgD-binding fragment having an amino acid sequence as described in SEQ ID NO 10.

In still another aspect the present invention relates to a vaccine containing an immunogenic and adhesive fragment of a surface exposed protein of *Moraxella catarrhalis* as defined above, preferably a vaccine containing an immunogenic and adhesive fragment having an amino acid sequence as described in SEQ ID NO 8.

In one preferred embodiment said vaccines are combined with another vaccine and in another preferred embodiment said vaccines are combined with an immunogenic portion of another molecule.

In one aspect the present invention relates to a plasmid or phage comprising a DNA sequence, which codes for a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants thereof, or an immunogenic or IgD-binding fragment of said protein or variants.

In another aspect the present invention relates to a plasmid or phage comprising a DNA sequence, which codes for a an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, preferably a plasmid or phage comprising a DNA sequence, which codes for a an immunogenic or IgD-binding fragment having an amino acid sequence as described in SEQ ID NO 10.

In still another aspect the present invention relates to a plasmid or phage comprising a DNA sequence, which codes for an immunogenic and adhesive fragment of a surface exposed protein as defined above, which fragment can be detected in *Moraxella catarrhalis* and has a capacity of selectively binding erythrocytes and epithelial cells or naturally occurring or artificially modified variants of said fragment, preferably a plasmid or phage comprising a DNA sequence, which codes for a an immunogenic and adhesive fragment having an amino acid sequence as described in SEQ ID NO 8.

In yet another aspect the present invention relates to a non human host comprising at least one plasmid or phage as defined above, and capable of producing said protein or variants, or said immunogenic or IgD-binding fragment of said protein or variants, or said immunogenic and adhesive fragment of said protein, which host is chosen among bacteria, yeast and plants. In one embodiment the host is *E. coli*.

In one aspect the present invention relates to a recombinant DNA molecule comprising a DNA sequence coding for a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants thereof, or for an immunogenic or IgD-binding fragment of said protein, or variants, which DNA sequence is fused to another gene.

In another aspect the present invention relates to a recombinant DNA molecule comprising a DNA sequence coding for an immunogenic or IgD-binding fragment of a surface exposed protein, which fragment can be detected in *Moraxella catarrhalis* and has a capacity of selectively binding membrane bound or soluble IgD, or naturally occurring or artificially modified variants thereof, which DNA sequence is fused to another gene, preferably a recombinant DNA molecule comprising a DNA sequence coding for an immunogenic or IgD-binding fragment having an amino acid sequence as described in SEQ ID NO 10.

In still another aspect the present invention relates to a recombinant DNA molecule comprising a DNA sequence coding for an immunogenic and adhesive fragment of a surface exposed protein as above, which fragment can be detected in *Moraxella catarrhalis* and has a capacity of selectively binding erythrocytes and epithelial cells, or naturally occurring or artificially modified variants of said fragment, which DNA sequence is fused to another gene, preferably a recombinant DNA molecule comprising a DNA sequence coding for an immunogenic and adhesive fragment having an amino acid sequence as described in SEQ ID NO 8.

In yet another aspect the present invention relates to a plasmid or phage comprising said fused DNA sequence as defined above.

In a further aspect the present invention relates to a non-human host comprising at least one plasmid or phage as defined above, which host is chosen among bacteria, yeast and plants. In one embodiment the host is *E. coli*.

In one aspect the present invention relates to a fusion protein or polypeptide, in which a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants thereof, or an immunogenic or IgD-binding fragment of said protein or variants, is combined with another protein by the use of a recombinant DNA molecule as defined above.

In another aspect the present invention relates to a fusion protein or polypeptide, in which an immunogenic or IgD-binding fragment of a surface exposed protein, which fragment can be detected in *Moraxella catarrhalis*, which has a capacity of selectively binding membrane bound or soluble IgD, or naturally occurring or artificially modified variants thereof, is combined with another protein by the use of a recombinant DNA molecule as defined above.

In still another aspect the present invention relates to a fusion protein or polypeptide in which an immunogenic and adhesive fragment of a surface exposed protein as defined above, which fragment can be detected in *Moraxella catarrhalis* and has a capacity of selectively binding erythrocytes and epithelial cells, or naturally occurring or artificially modified variants of said fragment, is combined with another protein by the use of a recombinant DNA molecule as defined in above.

In yet another aspect the present invention relates to a fusion product, in which a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants of said protein, or an immunogenic or IgD-binding fragment of said protein or variants, is covalently or by any other means bound to a protein, carbohydrate or matrix.

In a further aspect the present invention relates to a fusion product in which an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, is covalently or by any other means bound to a protein, carbohydrate or matrix.

In still another aspect the present invention relates to a fusion product in which an immunogenic and adhesive fragment of a surface exposed protein as defined above, which fragment can be detected in *Moraxella catarrhalis* and has a capacity of selectively binding erythrocytes and epithelial cells, or naturally occurring or artificially modified variants of said fragment, is covalently, or by any other means, bound to a protein, carbohydrate or matrix. Preferably, a fusion product in which an immunogenic or IgD-binding fragment, having an amino acid sequence described in SEQ ID NO 10, is covalently, or by any other means, bound to a protein, carbohydrate or matrix. Preferably, a fusion product in which an immunogenic and adhesive fragment, having an amino acid sequence described in SEQ ID NO 8, is covalently, or by any other means, bound to a protein, carbohydrate or matrix.

In one aspect the present invention relates to a method of detecting IgD using a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants of said protein, or an immunogenic or IgD-binding fragment of said protein or variants, optionally labelled and/or bound to a matrix.

In a further aspect the present invention relates to a method of detecting IgD using an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, optionally labelled and/or bound to a matrix.

In another aspect the present invention relates to a method of detecting IgD using an immunogenic or IgD-binding fragment of a surface exposed protein of *Moraxella catarrhalis*, having an amino acid sequence as described in SEQ ID NO 10, and a capacity of selectively binding membrane bound or soluble IgD, or naturally occurring or artificially modified variants of said fragment, optionally labelled and/or bound to a matrix.

In a further aspect the present invention relates to a method of separating IgD using a surface exposed protein of *Moraxella catarrhalis*, said protein an amino acid sequence as shown in SEQ ID NO 1, an apparent molecular weight of 200 kDa and a capacity of selectively binding membrane bound or soluble IgD, or naturally occurring or artificially modified variants of said protein, or an immunogenic or IgD-binding fragment of said protein or variants, optionally bound to a matrix.

In yet another aspect the present invention relates to method of separating IgD using an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, optionally bound to a matrix.

In another aspect the present invention relates to a method of separating IgD using an immunogenic or IgD-binding fragment of a surface exposed protein of *Moraxella catarrhalis*, having an amino acid sequence as described in SEQ ID NO 10, and a capacity of selectively binding membrane bound or soluble IgD, or naturally occurring or artificially modified variants of said fragment, optionally labelled and/or bound to a matrix.

In one aspect the present invention relates to a method of isolation of a surface exposed protein of *Moraxella catarrhalis*, said protein having an amino acid sequence as shown in SEQ ID NO 1, an apparent molecular weight of 200 kDa and a capacity of selectively binding membrane bound or soluble IgD, or naturally occurring or artificially modified variants of said protein, or an immunogenic or IgD-binding fragment of said protein or variants. Said method comprises the steps:
  a) subjecting a suspension of *Moraxella catarrhalis* to an extraction process by adding a zwitterionic or non-ionic detergent, optionally in the presence of EDTA;
  b) applying the extract comprising the IgD-binding protein of *Moraxella catarrhalis* from step a) to an adsorption column;
  c) eluating the IgD-binding protein; and
  d) separating the IgD-binding protein.

In another embodiment the concentration of the detergent in step a) of the method is within the range 0.1-5%, preferably 3%.

In yet another aspect the present invention relates to a method for treatment of an autoimmune disease comprising extra corporal circulation of the blood trough a material comprising a surface exposed protein as defined above, or a fragment thereof as defined above, for removal of IgD from the blood.

In one aspect the present invention relates to a purified antibody which is specific to an immunogenic portion of a surface exposed protein *Moraxella catarrhalis*, said protein having an amino acid sequence as described in SEQ ID NO 1, an apparent molecular weight of 200 kDa and a capacity of selectively binding membrane bound or soluble IgD, or naturally occurring or artificially modified variants thereof, or an immunogenic or IgD-binding fragment of said protein or variants.

In another aspect the present-invention relates to a purified antibody as described above, which is specific to an immunogenic or IgD-binding fragment as defined above, having a capacity of selectively binding membrane bound or soluble IgD, or naturally occurring or artificially modified variants of said fragment.

In still another aspect the present invention relates to a purified antibody as described above, which is specific to an immunogenic or adhesive fragment as defined above, having a capacity of binding erythrocytes and epithelial cells.

PBLs were isolated from heparinized human blood using Lymphoprep one-step gradients. Lymphocytes ($2.5 \times 10^5$) were incubated with the appropriate anti-bodies, washed and further incubated with MID-FITC (10 μg/ml). All incubations were performed on ice and after final washings, PBLs were analysed by flow cytometry. In this particular experiment, 68% of the total lymphocyte population was gated and analysed. Less than 2% of the cells were labeled when isomatched mAbs were included as negative controls. A pre-immune rabbit serum did not significantly block MID-FITC binding to the IgD BCR (not shown). An experiment with a typical donor out of three separate ones analysed is shown.

Figure 5:
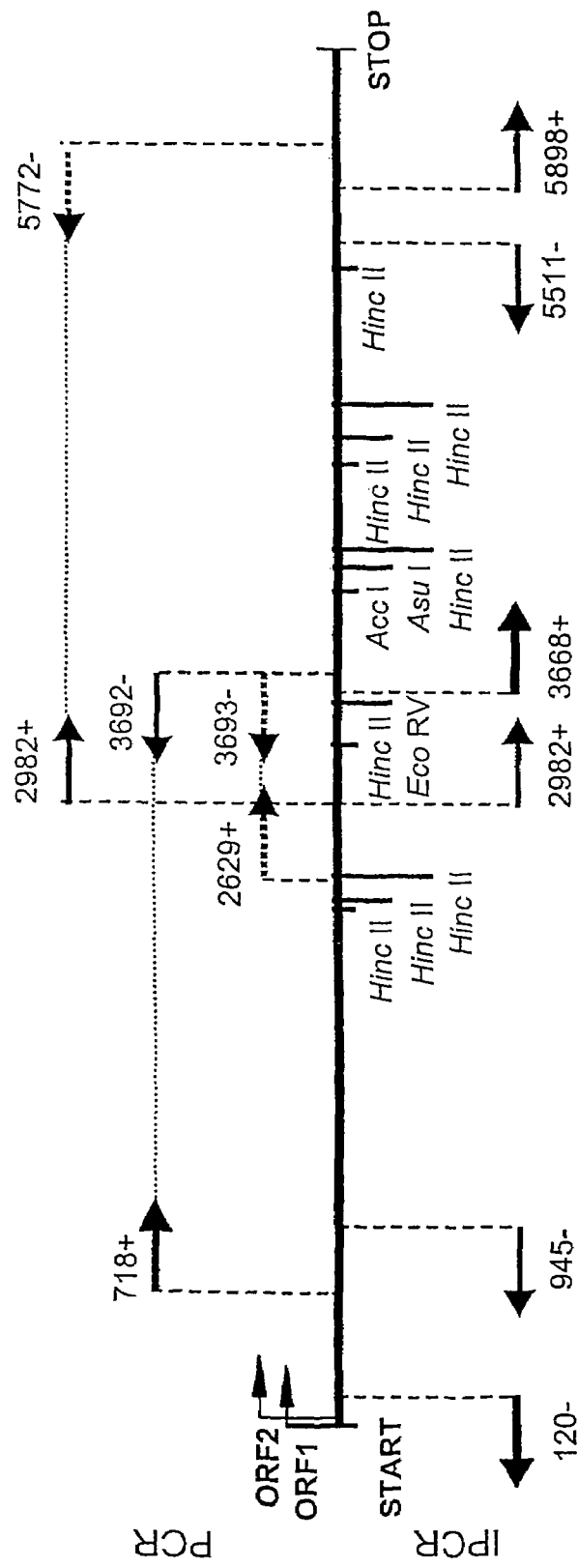

FIG. 5. Schematic map of the mid gene showing the cloning strategy. Oligonucleotide primers used for DNA amplification are indicated by arrows placed above (PCR) and below (inverse PCR [IPCR]) the relevant sequences. Degenerated primers based upon the amino acid sequences outlined in Table II and specific primers are shown by broken and solid lines, respectively.

FIG. 6. Nucleotide sequence (nucleotides 106-6889 of SEQ ID NO: 2) of the mid gene from *M. catarrhalis* Bc5 together with the deduced amino acid sequence (SEQ ID NO: 1). Putative −35, −10 regions, a possible ribosome binding site (RBS), inverted repeat, the predicted signal peptide, and two alternative start-codons at amino acid positions 1 and 17 are indicated. The stop-codon and the inverted repeat is also shown.

FIG. 7. The degrees of identity and similarity between MID isolated from five *M. catarrahlis* strains and UspA1 and A2 from ATCC 25238 are demonstrated. The identity and similarity were calculated using the software Needle.

FIG. 8. Comparison of the amino acid sequence of MID (SEQ ID NO: 1) with the protein presented in U.S. Pat. No. 5,808,024 (SEQ ID NO: 16).

Figure 9:
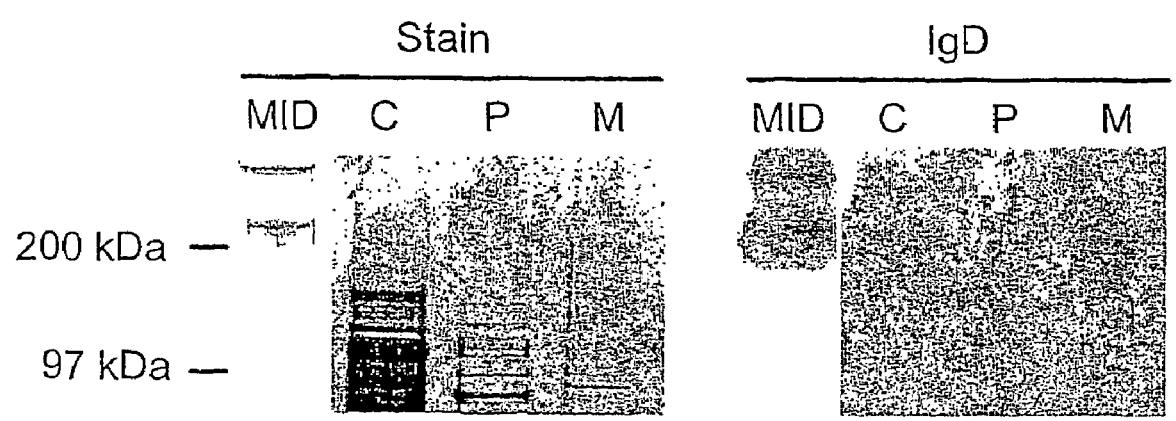

FIG. 9. Recombinantly expressed MID retained its IgD-binding capacity. The left panel shows a Coomassie brilliant blue stained gel and the right panel a Western blot probed with human IgD. Native MID protein (MID) was run and compared to cytoplasmic (C), periplasmic (P), and membrane (M) fractions. Numbers on the left indicate a molecular weight standard. *E. coli* BL21DE3 containing pET16-MID were induced for 4 h by IPTG. Cellular fractions were collected and proteins were separated by two SDS-PAGE that was run in parallel and either stained with Coomassie brilliant blue or blotted onto an Immobilon-P membrane. The membrane was probed with human IgD followed by incubation with a horseradish peroxidase-conjugated secondary antibody.

Figure 10:
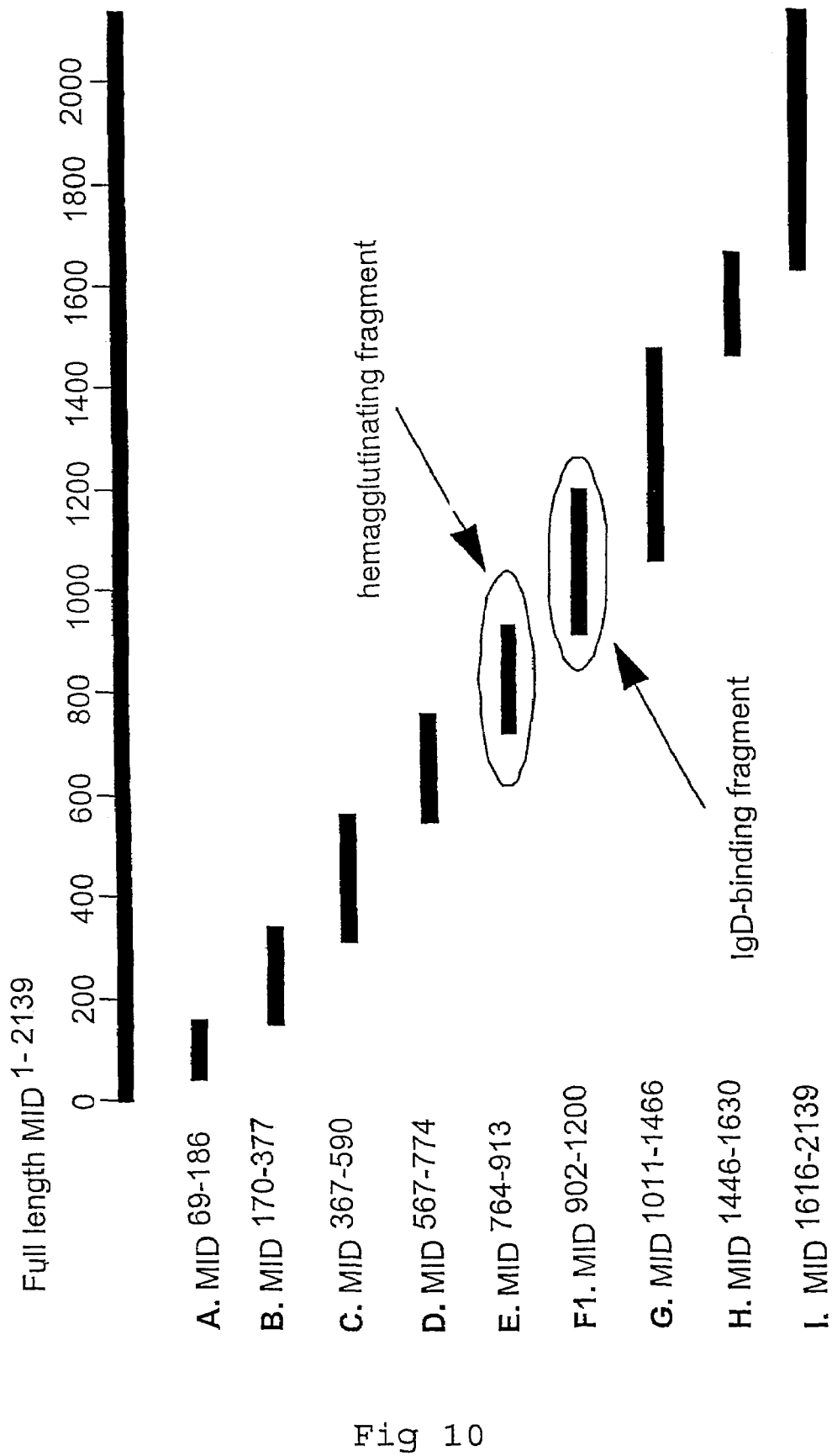

FIG. 10. MID764-913 (fragment E) and MID902-1200 (fragment F) is responsible for erythrocyte hemagglutination and IgD-binding, respectively. A series of truncated MID proteins (designated A to I) were manufactured. Recombinant proteins containing histidine tags in their C-terminals (A to H) or fused with maltose binding protein (I) were produced in *E. coli* and purified on nickel and amylose resin columns, respectively.

Figure 11:
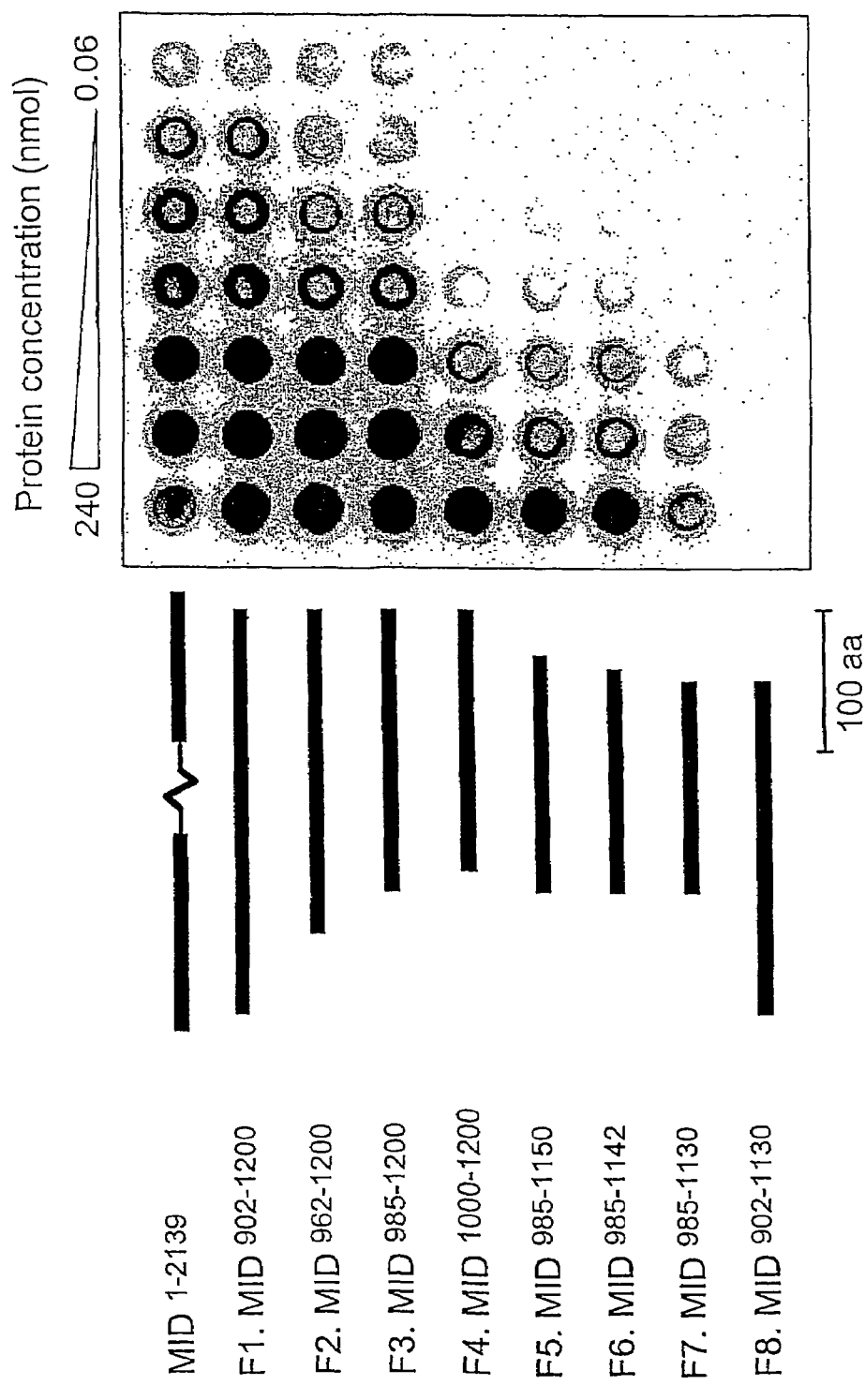

FIG. 11. MID962-1200 (fragment F2) has a conserved IgD-binding capacity compared with full length MID1-2139. Equimolar concentrations (range 240 to 0.06 nmol) of purified full length MID1-2139 and 8 truncated MID fragments (F1 to F8) were analysed for IgD-binding by dot blots. The proteins MID902-1130 (F8), MID985-1130 (F7), and MID1000-1200 (F4) did not attract IgD, whereas all other fragments bound IgD. DNA encoding for the various truncated MID proteins were cloned into the expression vector pET26b(+) and produced in *E. coli*. The recombinant proteins containing His-tags were purified and dot blotted onto a nitrocellulose membrane. The membrane was probed with human IgD followed by secondary HRP-conjugated polyclonal antibodies that were used for detection.

Figure 12:
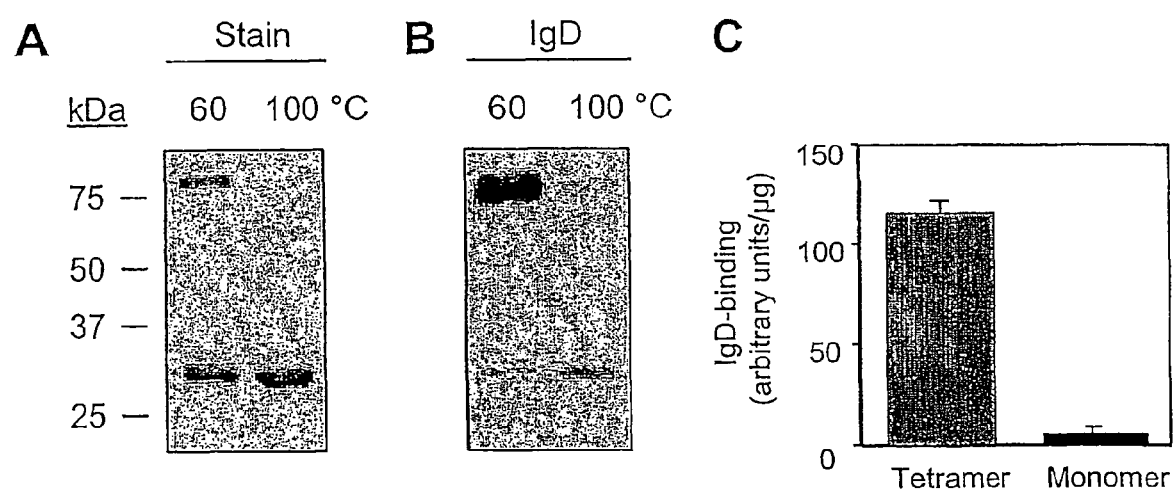

FIG. 12. A tetrameric structure of MID962-1200 (F2) is a prerequisite for optimal IgD-binding. (A), SDS-PAGE of MID962-1200 after treatment at 60° C. separates monomers and tetramers. After heat treatment at 100° C. monomers only can be detected. (B), Corresponding Western blot with IgD as probe reveals weak IgD-binding to monomers. (C), Mean IgD-binding to tetramers and monomers, respectively in 6 different experiments. IgD-binding is shown as arbitrary units/μg protein. MID962-1200 was treated in SDS-sample buffer at 60° C. or 100° C. for 10 min, and subjected to SDS-PAGE and Western blot analysis. The resulting Coomassie-stained gel and Western blot were analysed by densitometry. The percentage of protein migrating as tetramer or monomer was calculated and compared with the IgD-binding capacity.

Figure 13:
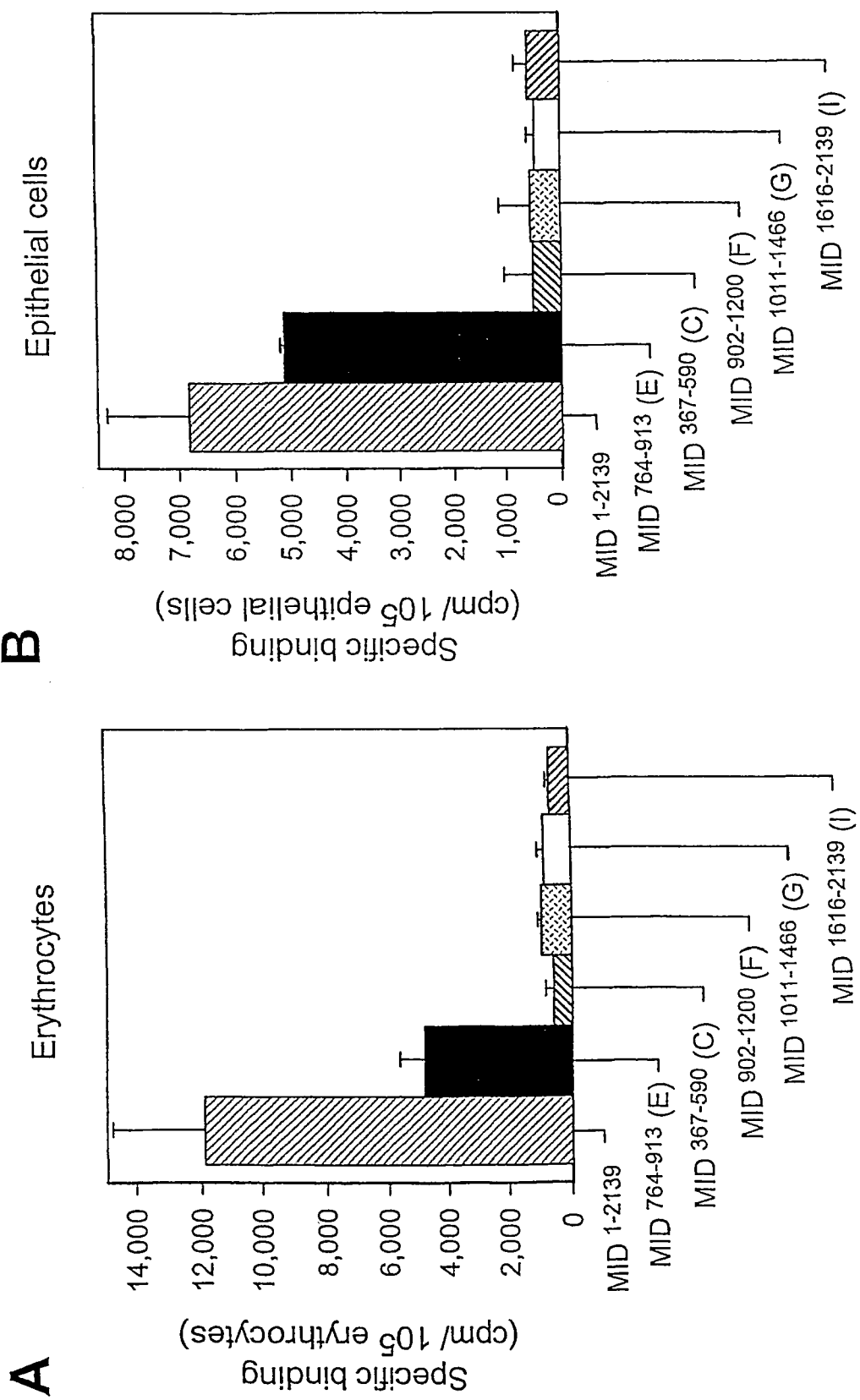

FIG. 13. [125I]-labelled recombinant MID764-913 (fragment E) is specifically attracted to erythrocytes and epithelial cells. [125I]-labelled MID and a series of truncated [125I]-MID fragments (C, E, F, G, and I) were added to human erythrocytes (A). The recombinant [125I]-labelled MID fragments were also added to epithelial cells (B). All truncated MID proteins (except fragment I) were produced in *E. coli* followed by purification on nickel resins. Fragment I was a fusion protein with MBP and consequently purified on an amylose resin. The recombinant proteins were labelled with [125I] and added to erythrocytes or the epithelial cell line A549. After several washings, bound radioactivity was measured in a γ-counter. Data are presented as mean values of 2 experiments with duplicates. Error bars indicate SD.

Figure 14:
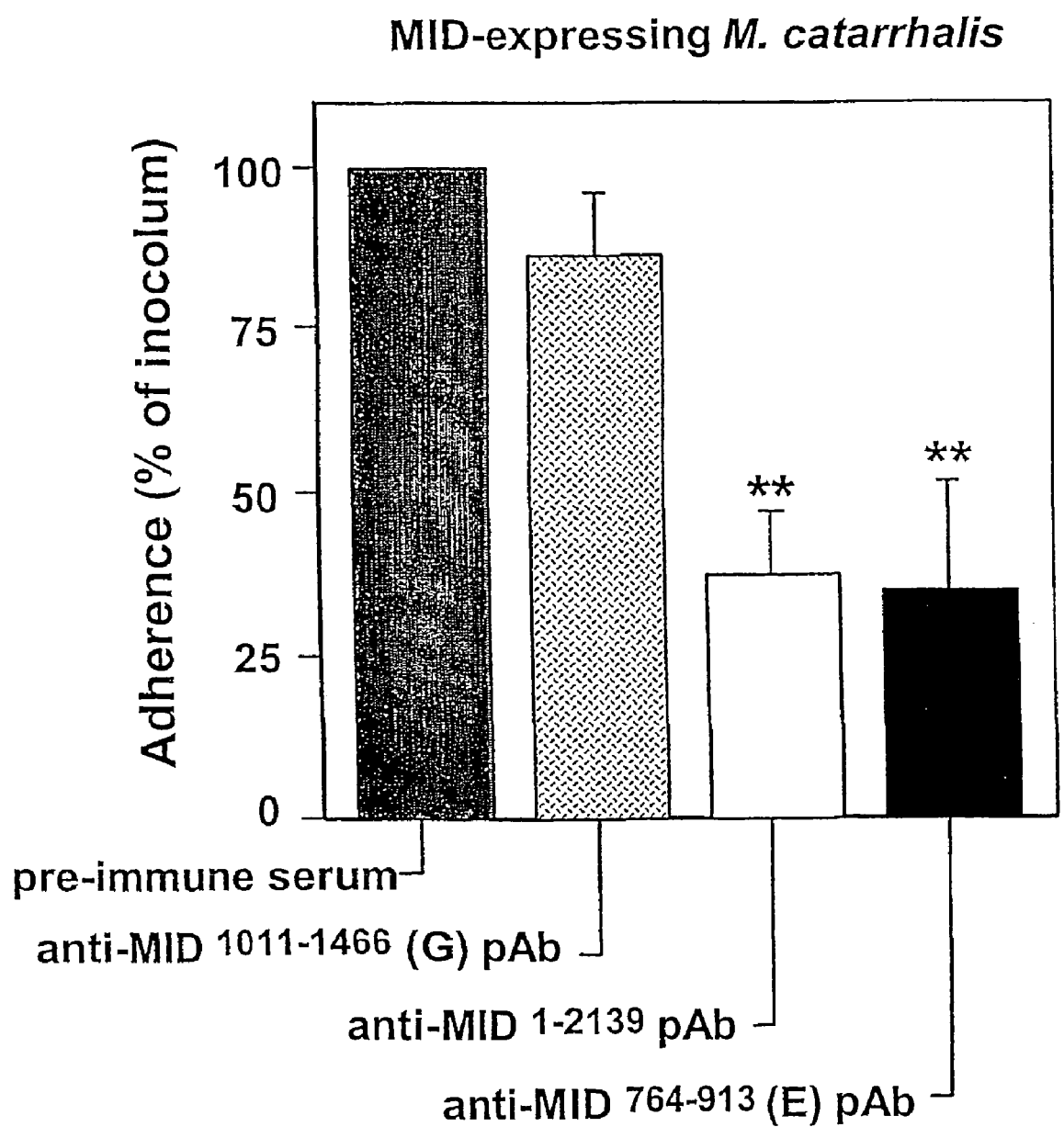

FIG. 14. Adhesion of MID-expressing *M. catarrhalis* to epithelial cells depends on the amino acid residues MID764-913 (fragment E). A decreased adhesion to epithelial cells was observed with MID-expressing bacteria coated with rabbit anti-MID1-2139 or anti-MID764-913 polyclonal antibodies compared to a pre-immune serum or anti-MID1011-1446 (fragment G) pAb. Bacteria were preincubated with the pre-immune serum or specific antisera for 1 h at 4° C. Bacteria were added to the epithelial cells followed by centrifugation and incubation for 30 min at 37° C. After washings, cells were treated with trypsin-EDTA and the suspensions were plated on blood agar plates. Colony forming units were counted after an overnight incubation. The adherence ratio (cfu added/cfu adhered) was calculated. Results are shown as mean values of 4 separate experiments with duplicates. Error bars indicate SD. * $P \leq 0.001$,  $P \leq 0.01$ and * $P \leq 0.05$.

DESCRIPTION OF THE INVENTION

MID is not identical to previously well characterized outer membrane proteins of *M. catarrhalis*. It is not recognized by monoclonal antibodies derived against the UspA or CopB outer membrane antigens. MID also has a different migration pattern in SDS-PAGE and a different composition as shown by amino acid and DNA sequence analysis. MID appeares as a 200 kDa band in accordance with the Mw from the deduced amino acid sequence, but also as an extra band with an estimated molecular mass of more than 1,000 kDa. The extra band indicates that native MID is an oligomeric complex in a similar fashion as UspA (11). This is further supported by the fact that MID was eluted immediately after the void volume from a Sephacryl. S-400 column with a fractionation range of up to −8,000 kDa. The amino acid sequences for MID shows 11.1 and 6.7% identity, respectively, with the USPA1 and USPA2 outer membrane proteins from *M. catarrhalis* (FIG. 7).

In a recent patent publication, an outer membrane protein of *M. catarrhalis* with a molecular mass of approximately 200 kDa was isolated (12). A sequence encoding a protein of approximately 200 kDa was also provided. However, that protein sequence is not identical to the sequence provided by us and shows only 45.9 to 54.4% identity with MID (FIG. 7). The protein was shown to be immunogenic, but no further biological functions were presented. In addition, a 200 kDa protein is associated with hemagglutinating *M. catarrhalis* (13,14).

Experimental Part

The present investigation describes the isolation, purification, characterization, cloning and expression of the novel Ig-binding protein named MID of *M. catarrhalis*, which has affinity for human IgD, of an immunogenic or IgD-binding fragment of said surface exposed protein, and of an immunogenic and adhesive fragment of said surface exposed protein.

MATERIALS AND METHODS

Bacteria and Plasmids

*M. catarrhalis*, strain Bc5, was a clinical isolate from a nasopharyngeal swab culture at our Department. 118 strains isolated from blood, nasopharynx, and sputum were obtained from Sweden, Denmark, Finland, Hungary, Japan, and USA. Sequenced strains and plasmids used for expression are shown in Table I.

TABLE I

Bacterial strains and plasmids used in this study

| Strains or plasmid | Description (site of isolation) | Reference or source |
| --- | --- | --- |
| Strains | | |
| DH5α | *E. coli* | Novagen |
| BL21DE3 | *E. coli* | Novagen |
| BBH17 | *M. cararrhalis* (sputum) | Christensen (Denmark) |
| Bc5 | *M. cararrhalis* (nasopharynx) | Dept. Clinical Microbiology, Malmö, Sweden |
| NCTC 4103 | *M. cararrhalis* (nasopharynx) | CCUG (Gothenburg, Sweden) |
| RH1 | *M. cararrhalis* (blood) | Christensen (Denmark) |
| RH4 | *M. cararrhalis* (blood) | Christensen (Denmark) |
| Plasmid | | |
| pET16 (b) | Expression vector | Novagen |
| pET16-MID | PET16 (b) with the ORF of mid | This study |

Bacteria were grown overnight in Nutrient Broth (Oxoid, Basingstoke Hampshire, England), harvested and washed in phosphate-balanced saline (PBS), pH 7.2 by centrifugation.

Immunoglobulins, Sera and Other Proteins

The Ig preparations IgG1 (κ), IgG1(λ), IgG2(κ), IgG2(λ), IgG3(κ), IgG3(λ), IgG4(κ), IgG4(λ), IgA1(κ) IgA1(λ), IgA2 (κ), IgA2(λ), IgM (κ), IgM(λ), IgD(κ), IgD(λ) and IgE(κ) were all of human origin and purchased from The Binding Site (Birmingham, England). IgD myeloma sera IgD(κ) and IgD(λ) were from the same company and IgD-standard serum OTRD 02/b3 was from Behringwerke AG (Marburg, Germany). Myeloma sera IgD(λ)A, IgD(λ) B, IgG A, IgG B, IgG C, IgM, IgA A and IgA B were obtained from the Department of Clinical Chemistry, Malmö, Sweden. The concentration of respective immunoglobulins was according to the suppliers.

Antibodies

Horseradish peroxidase (HRP)-conjugated goat anti-human IgD was from Biosource (Camarillo, Calif.). Fluoresceinisothiocyanate (FITC)-conjugated mouse anti-human IgD, unlabelled rabbit anti-human IgD, and HRP-labelled rabbit anti-mouse Ig were purchased from Dakopatts (Gentofte, Denmark). Goat anti-human IgD and HRP-conjugated rabbit anti-human polyvalent immunoglobulins was from Sigma (St. Louis, Mo.). Phycoerythrin (RPE)-conjugated mouse anti-human CD3 and CD19 were from Becton Dickinson (San José, Calif.). Mouse monoclonal antibodies 17C7 (UspA) and 10F3 (CopB) were kindly provided by Dr. Eric J. Hansen, Department of Microbiology, University of Texas (Dallas, Tex.).

Antisera

Rabbits were immunized intramuscularly with 200 μg of purified MID (Forsgren et al., 2001), recombinant MID fragments, or recombinant UspA1 emulsified in complete Freunds adjuvans (Difco, Becton Dickinson, Heidelberg, Germany) and boosted on days 18 and 36 with the same dose of protein in incomplete Freunds adjuvans. Blood was drawn 2 to 3 weeks later. The anti-UspA1 polyclonal antibodies reacted with both recombinant UspA1 and UspA2 as examined by Western blots.

SDS-PAGE and Detection of Proteins on Membranes (Western Blot)

SDS-PAGE was run using a commercial electrophoresis system consisting of 10% Bis-Tris gels with running (MES), sample (LDS), and transfer buffer as well as a blotting instrument (Novex, San Diego, Calif.). Briefly, samples were boiled for 10 min followed by electrophoresis at room temperature using Protein II vertical slab electrophoresis cells (Novex) at 150 constant voltage. Gels were stained with Coomassie Brilliant Blue R-250 (Bio-Rad, Sundbyberg, Sweden). In addition, electrophoretical transfer of protein bands from the gel to an immobilon-P membrane (Millipore, Bedford, Mass.) was carried out at 30 V for 2-3 h. After transfer, the immobilon-P membrane was blocked in PBS with 0.05% Tween 20 (PBS-Tween) containing 5% milk powder. After several washings in PBS-Tween, the membrane was incubated for 1 h in room temperature with purified IgD myeloma protein (0.5 μg/ml, hu IgD(κ) myeloma; The Bindingsite, Birmingham, UK) in PBS-Tween including 2% milk powder. HRP-conjugated goat anti-human IgD diluted 1/1000 in the same buffer was added after several washings in PBS-Tween. In some experiments, IgD myeloma protein was replaced by myeloma protein of other immunoglobulin classes and HRP-labeled anti-human polyvalent immunoglobulins (Sigma) was used as secondary layer. Mouse mAbs 17C7 and 10F3 were used to detect *Moraxella* outer membrane proteins UspA1, 2 and Cop B, respectively (7,8). In these experiments, HRP-labeled rabbit anti-mouse immunoglobulins were used as a secondary layer. After incubation for 40 min at room temperature and several additional washings in PBS-Tween, developement was performed with ECL Western blotting detection reagents (Amersham Pharmacia Biotech, Uppsala, Sweden). Western blots were analysed by a Personal Molecular Imager FX (Bio-Rad).

Enzyme Linked Immunosorbent Assay (ELISA)

ELISA was used to quantitate the immunoglobulin D-binding protein. Extracts of *M. catarrhalis* diluted in five-fold steps in 0.1 M Tris-HCl, pH 9.0 were added in 100 μl volumes to microtiter plates (F96 Maxisorb, Nunc-Immuno module, Roskilde, Denmark), which were sealed and incubated at 4° C. overnight. After washing the plate four times in PBS-Tween, blocking buffer PBS-Tween containing 1.5% ovalbumin, was added. The plate was incubated for 1 h at room temperature and further washed four times with PBS-Tween. IgD(κ) myeloma protein, 0.05 μg in 100 μl PBS-Tween containing 1.5% ovalbumin was added to each well and after incubation for 1 h at room temperature the plate was washed four times with PES-Tween. After 1 h incubation with HRP-conjugated goat anti-human IgD diluted 1/1000 in the same buffer and subsequent washing with PBS-Tween, tetramethylbenzidine (20 mM) in 0.1 M potassium citrate solution, pH 4.25, mixed with hydrogen peroxide (final concentration 0.002%) was added. After 30 min, the enzymatic reaction was stopped by adding 2 M sulphuric acid. The optical density (OD) was then measured at 450 nm in an automated ELISA reader (Multiskan Plus, Labsystems, Finland)

Dot Blot Assay

Purified MID (0.0005-0.2 μg) in a volume of 100 μl in 0.1 M Tris-HCl, pH 9.0 were manually applied to nitrocellulose membranes (Schleicher & Schuell, Dessel, Germany) by using a dot blot apparatus (Schleicher & Schuell). After saturation, the membranes were incubated for 2 h at room temperature in PBS-Tween containing 1% ovalbumin and 5% milk powder and washed four times with PBS-Tween. Human myeloma protein 0.5 μg in 100 μl PBS-Tween was added and after 2 h of incubation, followed by several washings in PBS-Tween, HRP-labelled anti-human light chains (κ and λ) (Dakopatts) in dilution 1/200 was used as a secondary antibody. Development was performed as described above for the Western blots. In another set of experiments, dilutions of human myeloma sera in a volume of 100 μl in 0.1 M Tris-HCl, pH 9.0 was first applied to the membranes. After saturation, incubations, blocking, and washing steps were performed as described above. Thereafter, [$^{125}$I]-labeled protein MID probe (5 to 10×10$^5$ cpm/ml) in PBS-Tween was added. After overnight incubation, the membrane was washed four times with PBS-Tween, air dried, and exposed to Kodak CEA.C x-ray films at −70° C. using Kodak X-Omat regular intensifying screen (Eastman Kodak, Rochester, N.Y.).

Extraction of IgD-Binding Protein

*M. catarrhalis* bacteria (1-5×1011 colony forming units (cfu)/ml) were suspended in 0.05 M Tris-HCl-buffer (pH 8.8) containing 0.1-5% Empigen (Calbiochem Novabiochem, Bedford, Mass.). In some experiments Empigen was replaced by CHAPS (Sigma), n-Octyl-p-D-glucoside (Bachem, Budendorf, Switzerland) or Triton X-100 (Sigma). All these detergents at a concentration of 0.1-5% were tested with or without 0.01 M EDTA. The bacterial suspensions were mixed by magnetic stirring for 2 h at 37° C. After centrifugation at 8000×g for 20 min at 4° C., the supernatants were filtrated with sterile filters (0.45 μm; Sterivex-HV, Millipore).

Purification of IgD-Binding Protein

*M. catarrhalis* extract in 3% Empigen® was applied to a Q-sepharose column (Amersham Pharmacia Biotech) equilibrated with 0.05 M Tris-HCl (pH 8.8) containing 0.1% Empigen®. The column was eluted using a 0 to 1 M NaCl linear gradient in the same buffer. Fractions showing most IgD-binding activity as detected by ELISA and Western Blot were pooled, dialyzed in Spectraphor membrane tubes (molecular weight cut off 25,000; Spectrum, Laguna hills, CA) against 0.05 M Tris-HCl, pH 8.8, concentrated on YM100 disc membranes (molecular weight cut off 100,000; Amicon, Beverly, Mass.) and then applied to gel-chromatography. The gel-filtration of IgD-binding protein was done on a Sephacryl S-400 high resolution column (20 by 900 mm; Amersham Pharmacia Biotech), equilibrated with 0.05 M Tris-HCl, pH 8.8 containing 0.1% Empigen®. Fractions containing the strongest IgD-binding activity were concentrated and re-chromatographed as described above.

Peptide Cleavage and Amino Acid Sequence Analysis

Purified MID in 0.05 M Tris-HCl (pH 8.8) containing 0.1% Empigen® was treated with trypsin or chymotrypsin in an enzyme-protein-ratio of 1:10 at 37° C. overnight. The cleavage mixtures were subjected to SDS-PAGE and peptide bands transferred to Immobilon membranes were automatically sequenced or exposed to Western blot analysis as described above. In order to get an N-terminal sequence of the protein, deblocking of intact MID from a possible pyroglutamate group was attempted. Two different protocols were used to deblock both soluble and membrane-bound protein. Automated amino acid sequence analysis was performed with an Applied Biosystems (Foster City, Calif.) 470A gas-liquid solid phase sequenator with on-line detection of the released aminoacid phenylthiohydantoin derivatives by Applied Biosystems model 120A PTH analyser.

Labeling of Protein MID

Purified MID was radioiodinated ([$^{125}$I]; Amersham, Buckinghamshire, England) to high specific activity with lactoperoxidase. The preparations contained approximately 0.05 mol iodine per mol protein. FITC (Sigma) was conjugated to purified MID using a standard protocol. Briefly, MID (2 mg/ml) in 0.1 M carbonate buffer, pH 9.5, was incubated with 0.15 μg/ml FITC solubilized in DMSO. After 45 min at room temperature and constant stirring, the sample was diluted and subjected to a PD10 column (Pharmacia Biotech) pre-equilibrated with PBS, pH 7.4. The resulting MID-FITC was used for binding studies.

DNA Isolation and Sequencing

Genomic DNA was extracted from five *M. catarrhalis* strains (see Table I) using a genomic DNA preparation kit (Qiagen, Hilden, Germany) and was subsequently used as template for amplification of the MID gene by PCR. Degenerate primers were synthesized according to the amino terminal sequences of the four peptide fragments (Table II).

TABLE II

Amino acid sequences derived from highly purified MID after protease digestions. (SEQ ID NOS: 12-15, respectively in order of appearance).

| Peptide sequence | Protease |
| --- | --- |
| TAQANTESSIAVG | Trypsin |
| GNTATNFSVNSGDDNALIN | Trypsin |
| QGINEDNAFVKGLEK | Trypsin |
| PSTVKADN | Chymotrypsin |

In some of the PCR reactions (High Fidelity PCR System; Roche, Bromma, Sweden), specific primers were used in combination with the degenerate ones. DNA sequences flanking the central region of the gene, where the peptide fragments originated from, were isolated using inverse PCR (IPCR). Briefly, genomic DNA was cleaved with the following restriction enzymes used separately; EcORV, SphI and PstI for the isolation of the start codon, and AccI, AsuI and finally HincII for the isolation of the stop codon sequences. The resulting fragments were religated upon themselves (Rapid DNA Ligation Kit; Roche) and the DNA was used in IPCR. To amplify the start and stop codon areas of the gene, specific primers were designed and used in a long template PCR (LTPCR) (Expand Long Template PCR System; Roche). All PCR products were cloned into pPCR-Script-Amp (Stratagene, La Jolla, Calif.) and sequenced using the Big Dye Cycle Sequencing Ready Reaction kit (Applied Biosystems, Warrington, England). Primers for amplification of genomic DNA were designed using the Oligo Primer Analysis software (Molecular Biology Insights, Cascade, Co). The signal peptide was deduced using the SignalP V1.1 World Wide Web Prediction Server Center for Biological Sequence Analysis (http://www.cbs.dtu.dk/services/SignalP/)

PCR Amplification of the Mid Gene

The complete 6.4 kb open reading frame of the mid gene was amplified by PCR using *M. catarrhalis* BcS strain genomic DNA as template. The oligonucleotide primers containing BamHI restriction enzyme recognition sequences were 5'-cgggatccgatggccgtggcggaatatgcc-3' (primer A, SEQ ID NO 3) and 5'-cgcggatccgaaaagtgaaaacctgcaccaactgctgc-3' (primer B, SEQ ID NO 4) generating a PCR product of 6391 base pairs. BamHI-digested insert was ligated into pET16(b) and the resulting plasmid pET16-MID was transformed into DH5α. Both strands of the cloned PCR product were sequenced.

To examine the full length mid gene in other *M. catarrhalis* strains, the primers A and B were used. In addition, primers used for narrowing down the sequence encoding the signal peptide were either primer A or 5'-tgtcagcatgtatcattttttaagg-taaaccaccatg-3' (primer C; detecting the upper start codon, SEQ ID NO 5) in combination with 5'-catcaattgcgatatgtctgg-gatcttg-31 (primer D; located at a conserved region just outside the signal peptide, SEQ ID NO 6) generating 192- and 266-base pair long PCR products (using Bc5 genomic DNA as template), respectively. Furthermore, primer A or C in combination with 5'-cttcaccccatcagtgccatagacc-3' (primer E, SEQ ID NO 7) were used for confirming the existence of the mid gene resulting in 1355- and 1429-base pair long fragments, respectively. The expand long template PCR system was used in all reactions and conditions were as recommended by the manufacturer (Roche, Bromma, Sweden).

Expression of the Mid Gene Product in *E. coli* and Cell Fraction

To express the mid gene product, pET16-MID was transformed into the expression host BL21DE3, containing a chromosomal copy of the T7 RNA polymerase gene under lacUV5 control. The recombinant bacteria were grown in LB medium supplemented with 2% of glucose and ampicillin. Overexpression was achived by growing cells to logarithmic-growth phase at $OD_{600}$ of 0.6 followed by addition of 1 mM IPTG. After 4 h of induction, bacteria were sonicated according to a standard protocol and the resulting proteins were analysed by SDS-PAGE.

Localisation of recombinant protein from pET16-MID was carried out by osmotic shock as described. Briefly, broth cultures of induced and uninduced cells were harvested and resuspended in 30 mM Tris-HCl, pH 8, containing 20% sucrose. EDTA was added to a final concentration of 1 mM and the solution was slowly stired at room temperature for 10 min. After centrifugation at 10,000 g for 10 min at 4° C., cells were resuspended in ice-cold 5 mM $MgSO_4$ and stired for 10 min on ice. During this step, the periplasmic proteins were released into the buffer. The supernatant containing the periplasmic fraction was collected by centrifugation. Bacteria were completely lysed by lysozyme at a final concentration of 100 mg/ml followed by sonication. Finally, the soluble cytoplasmic and insoluble membrane fractions were collected.

Truncated MID-Derived Recombinant Proteins

The different truncated MID fragments designated A to I with their specific sizes and primers for generating the proteins are shown in FIG. 10. The open reading frame of the mid gene from *M. catarrhalis* Bc5 (in pET26-MID) (Forsgren et al., 2001) was used as template. All MID constructs, except for MID367-590 (C), were amplified by PCR using specific primers introducing BamHI and HindIII restriction enzyme sites. Due to an internal HindIII restriction enzyme site in fragment C, an XhoI site was used instead of HindIII at the 3' end. All PCR products, except for MID1616-2139 (I), were cloned into pET26 (Novagen, Madison, Wis.). The PCR product encoding for the I fragment was cloned into pMAL-c2 (New England Biolabs, Beverly, Mass.). To avoid presumptive toxicity, the resulting plasmids were first transformed into the non-expressing host *E. coli* DH5α. Thereafter, plasmids encoding for fragments A to D, G and H were transformed into *E. coli* BL21(DE3), whereas the host BL21(DE3)-pLysS was used for vectors containing fragments E and F. Both *E. coli* strains were incubated in the presence of kanamycin, whereas chloramphenicol also was supplemented when BL21(DE3)-pLysS transformants were used. Fragment I was expressed in DH5α. Bacteria were grown to mid-log phase followed by induction with 1 mM isopropyl-1-thio-β-D-galactoside (IPTG). After 3.5 h, transformants were sonicated and the overexpressed proteins were purified according to the manufacturers instructions. Resulting recombinant proteins having a histidine tag or fused to maltose binding protein were purified on resins containing nickel amylose, respectively. The concentrations of the eluted proteins were determined using the BCA Protein Assay Kit (Pierce). Thereafter, recombinant proteins were analysed by SDS-PAGE and Western blots.

Hemagglutination

Human erythrocytes were obtained from freshly drawn heparinized human blood. The erythrocytes were washed twice in PBS (pH 7.2) and suspended in PBS at a final concentration of 1%. Bacteria cultured in Nutrient Broth were harvested by centrifugation, washed and suspended to 1-2× 109/ml in PBS. Bacteria and erythrocyte suspension (50 µl of each) were mixed in round bottom microtiter plates (Sarstedt, Newton, N.C.). In some experiments, erythrocytes were mixed with MID-Sepharose or BSA-Sepharose in 150 µl PBS. Agglutination was read by the naked eye.

Cell Line and Adherence Assay.

The lung carcinoma cell line A549 (type II alveolar epithelial cells; CCL-185) was obtained from ATCC. The cells were cultured in RPMI 1640 medium (Gibco BRL, Life Technologies, Paisley, Scotland) supplemented with 10% fetal calf serum, 2 mM L-glutamine, and 12 µg/ml gentamicin (referred to as culture medium). On the day before adherence experiments, cells were harvested, washed twice in gentamicin-free RPMI 1640 and added to 12-well tissue culture plates (Nunc, Roskilde, Denmark) at a concentration of 1×104 cells/well in 2.0 ml gentamicin free culture medium. Cells were thereafter incubated overnight at 37° C. in 5% CO2. On the day of experiments, *M. catarrhalis* (−2×108) in PBS, 0.15% gelatin (Sigma) was inoculated onto the monolayers. In neutralization experiments with specific antisera, bacteria were preincubated with polyclonal antibodies (dilution 1/250). After 1 h at 4° C., bacteria were added to the epithelial cells. In all experiments, tissue culture plates were centrifuged at 3,000 g for 5 min and incubated at 37° C., 5% CO2. After 30 min, the infected monolayers were rinsed twice with PBS, 0.15% gelatin with gentle rocking to remove nonadherant bacteria and then treated with trypsin-EDTA (0.05% trypsin, 0.5 mM EDTA) to release them from the plastic support. Thereafter, the resulting cell/bacteria suspension was seeded to agar plates containing 1.1% isovitalex, 7.8% human blood, and finally 0.9% proteose peptone. Data was calculated from duplicate cultures.

Flow Cytometry Analysis

Human peripheral blood lymphocytes (PBLs) were isolated from heparinized blood from healthy donors by centrifugation on a step gradient of Ficoll-Isopaque (Lymphoprep; Pharmacia, Uppsala, Sweden). For flow cytometry analyses, a standard staining protocol was used with 0.5% BSA (w/v) in PBS as buffer. PBLs (2.5×105 in 100 µl) were labeled with anti-CD3 or anti-CD19 mAbs with or without FITC-conjugated anti-IgD mAb on ice for 30 min according to the manufacturer's instructions. In blocking experiments, lymphocytes were also pre-incubated with anti-IgD immunoglobulins for 30 min. After two washes, 10 µg/ml of purified FITC-conjugated MID was supplemented to the cells followed by incubation for 45 min on ice. After 4 final washes with excess PBS 0.5% BSA, 105 cells for each sample were analysed in an EPICS®XL-MCL flow cytometer (Coulter, Hialeah, Fla.). Where appropriate, rabbit and goat pre-immune sera and mouse IgG1 and IgG2a were included as negative controls (Dakopatts)

Results

Extraction and Purification of MID

Figure 1:
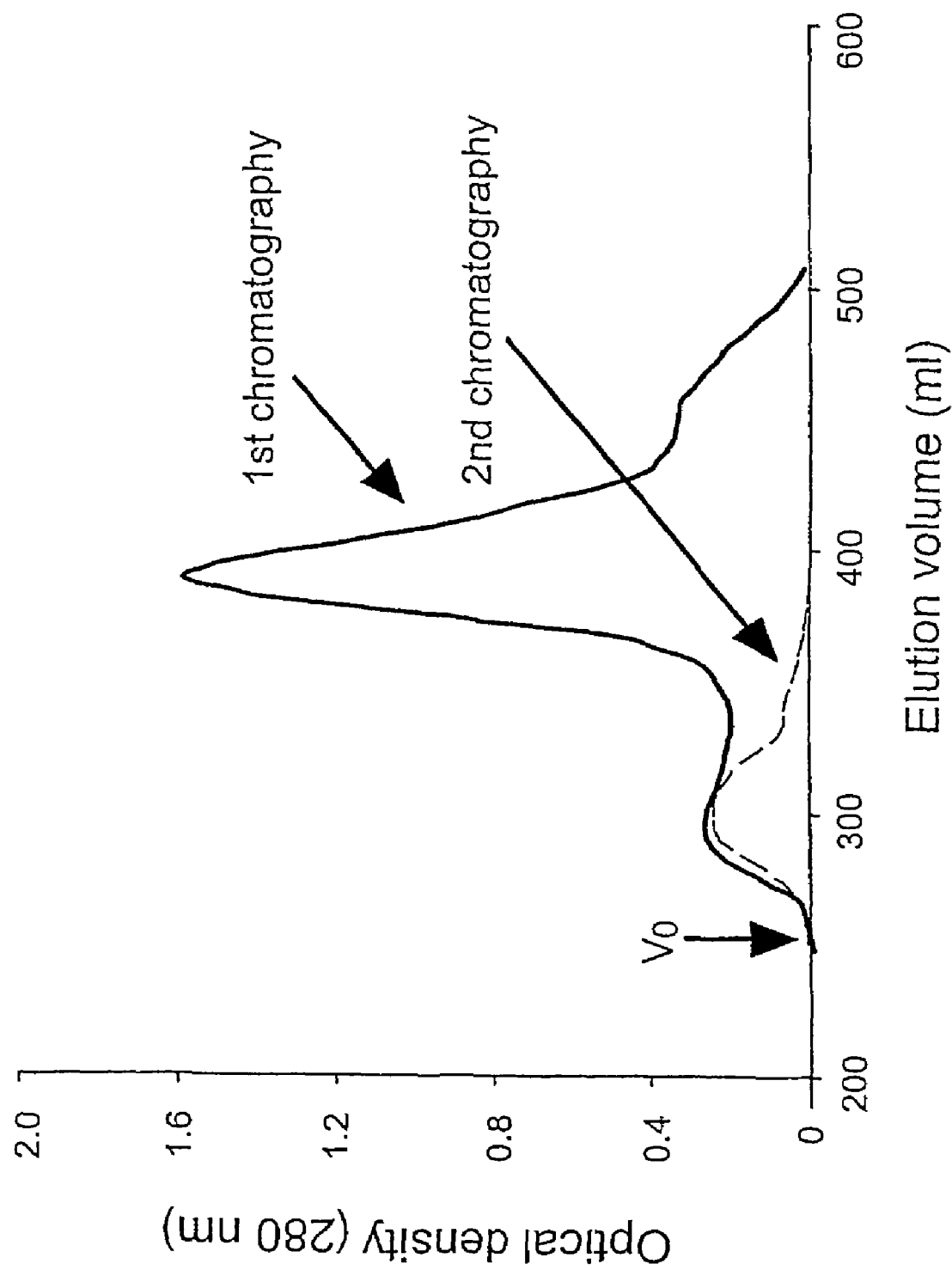
FIG. 1. Chromatography and rechromatography on a Sephacryl S-400 column of Empigen® soluble extract from *M. catarrhalis* after ion exchange chromatograpy. The solid line indicates protein content of the first chromatography and the broken line rechromatography of the first peak. Vo specifies the void volume.

Solubilization of MID was a major obstacle in the process of purification. Amongst several detergents tested, only Empigen® and n-Octyl-b-D glucoside alone at a final concentration of 3% solubilized MID from a suspension of *M. catarrhalis* efficiently as estimated by ELISA and Western blot. The two detergents were equally efficient. Triton X-100 alone did not solubilize MID, but Triton X-100 plus 0.01 M EDTA solubilized MID efficiently. C HAPS alone or CHAPS with EDTA or EDTA alone did not solubilize MID. In the following experiments, Empigen® extraction was used for solubilization and subsequent purification of MID. When the Empigen® extract of *M. catarrhalis* was applied to a Q-sepharose column, all IgD-binding material was eluted from the column with 0.1% Empigen® in 0.05 M Tris HCl, pH 8.8. No additional IgD-binding material could be eluted when a NaCl-gradient up to 1 M was applied to the same column. After concentration of the IgD-binding material obtained after separation on Q-sepharose, fractionation of the extract was achieved by gel filtration in the presence of 0.1% Empigen®on a Sephacryl S-400 column (FIG. 1). Most IgD-binding material was eluted in this first peak immediately after the void volume. MID was further purified by rechromatography of the first peak under the same conditions.

Figure 2:
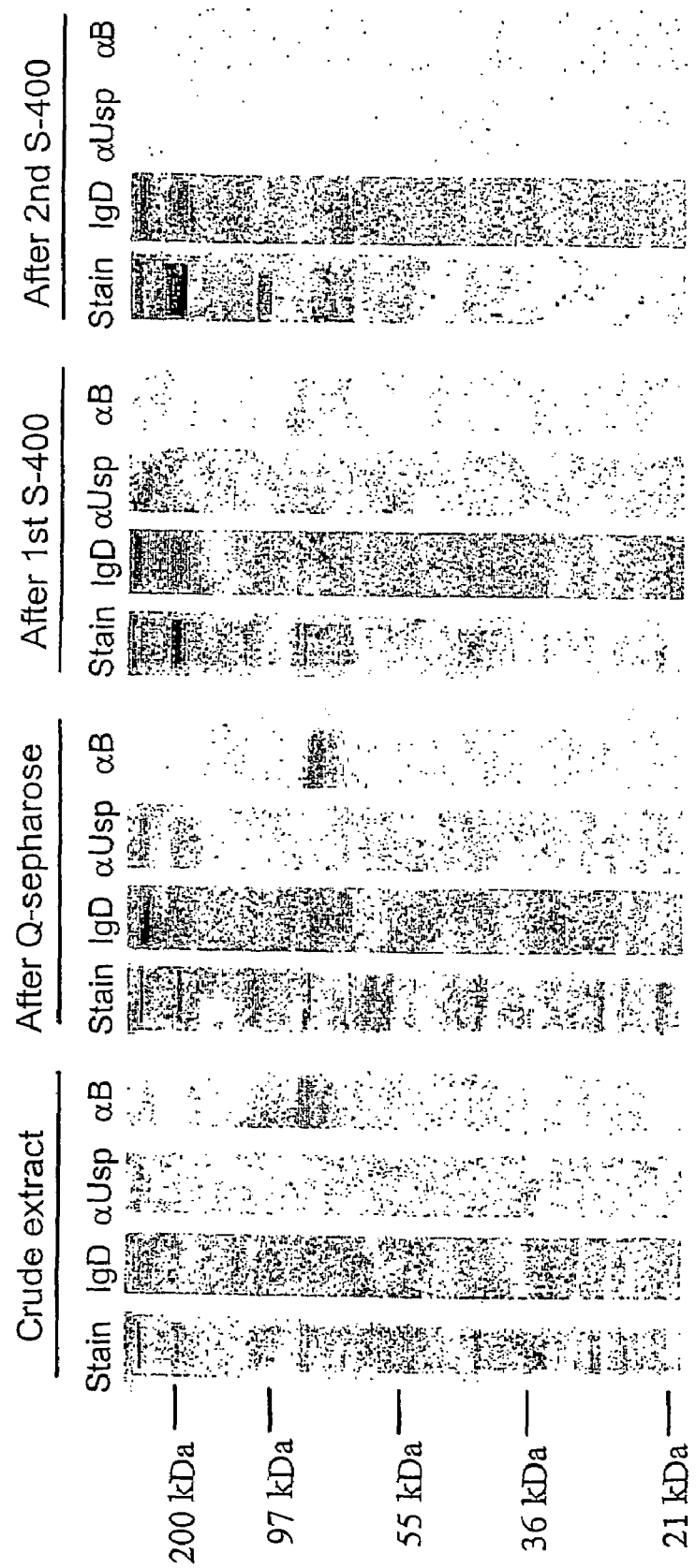
FIG. 2. Analysis on SDS-PAGE of fractions representing different purification steps of MID. The fractions are shown for crude extract in 3% Empigen®, after an ion-exchange chromatography on Q-sepharose column, and after the 1st and 2nd gelfiltrations on a Sephacryl S-400 column. Two gels were run simultaneously, one was stained with Coomassie blue (Stain) and one was blotted onto Immobilon-P membranes, probed with human IgD(κ) myeloma protein (IgD), anti-UspA (αUsp), or anti-CopB (αB) monoclonal antibodies followed by incubation with appropriate horseradish peroxidase-conjugated secondary antibodies. Molecular weights of marker proteins are indicated to the left.

FIG. 2 shows that after purification MID appeared as two bands, one 200 kDa-band and a second band with an apparent molecular mass of more than 1,000 kDa. Western blot experiments were performed to confirm that MID was not identical to the previously described outer membrane proteins UspA1 and 2 with an apparent molecular mass varying from 350 to 720 kD (8-10) or CopB with a molecular weight of 80 kDa. The crude Empigen® extract of *M. catarrhalis* or partly purified preparations of MID were subjected to SDS-PAGE, transferred to Immobilon filters and blotted with antibodies to those *Moraxella* proteins and also with human IgD. As can be seen in FIG. 2, MID (as revealed by IgD-binding) is not identical with the outer membrane proteins UspA and Cop B.

Three attempts were made to determine the amino-terminal amino acid sequence of purified MID. Approximately 1000 pmol of MID was applied each time in an automated amino acid sequencer. Inasmuch as no amino acid phenylthiohydantoin derivatives were obtained, the amino-terminal end of the singel MID polypeptide chain was probably blocked. It was recently determined that the moraxella UspA1 and UspA2 proteins, which are also resistant to Edman degradation, contained a pyroglutamyl residue that was removed by the treatment with pyroglutamate aminopeptidase. However, when MID purified from *M. catarrhalis* or recombinant MID was treated with this enzyme according to two different protocols (twice for each method) and then subjected to Edman degradation, no N-terminal amino acid sequence was obtained.

IgD-Binding Properties of MID

Crude Empigen® extracts of *M. catarrhalis* and highly purified MID subjected to SDS-PAGE and transferred to filters were exposed to highly purified commercially available Ig-preparations representing all human Ig-classes and subclasses (Table III).

TABLE III

Summary of Western Blot and dot blot analyses showing the binding specificity of highly purified commercially available myeloma immunoglobulin D preparations against a crude Empigen ® extract of *M. catarrhalis* and highly purified MID.

| Immunoglobulin | 200 kDa-protein in crude extract | Purified MID |
| --- | --- | --- |
| IgD(κ), IgD(λ) | + | + |
| IgG1(κ), IgG1(λ) | − | − |
| IgG2(κ), IgG2(λ) | − | − |
| IgG3(κ), IgG3(λ) | − | − |
| IgG4(κ), IgG4(λ) | − | − |
| IgA1(κ), IgA1(λ) | − | − |
| IgA2(κ), IgA2(λ) | − | − |
| IgM; (κ), IgM(λ) | − | − |
| IgE(κ) | − | − |

Only the two IgD preparations interacted with the MID-band in the 200 kDa-position in a similar fashion as shown for IgD in FIG. 2. When dot blot experiments were performed and purified MID in dilutions was first added to membranes and purified human myeloma proteins and secondary antibodies were subsequently applied, only the two IgD myelomas interacted with MID. One of the two myelomas detected as little as 0.001 µg of MID on the membrane. The specificity of the interaction between MID and IgD was further verified by using radiolabeled MID in other dot blot experiments In FIG. 3, it is demonstrated that MID effectively bound four IgD myeloma sera. A distinct reaction could be detected in the range 0.03-4 µg of IgD. For the IgD standard serum (B.W.) reactivity was seen at even lower concentrations (not shown). In contrast, 6 different Ig myeloma sera representing IgG, IgA and IgM showed no visible reaction with MID at 4 µg.

Figure 3:
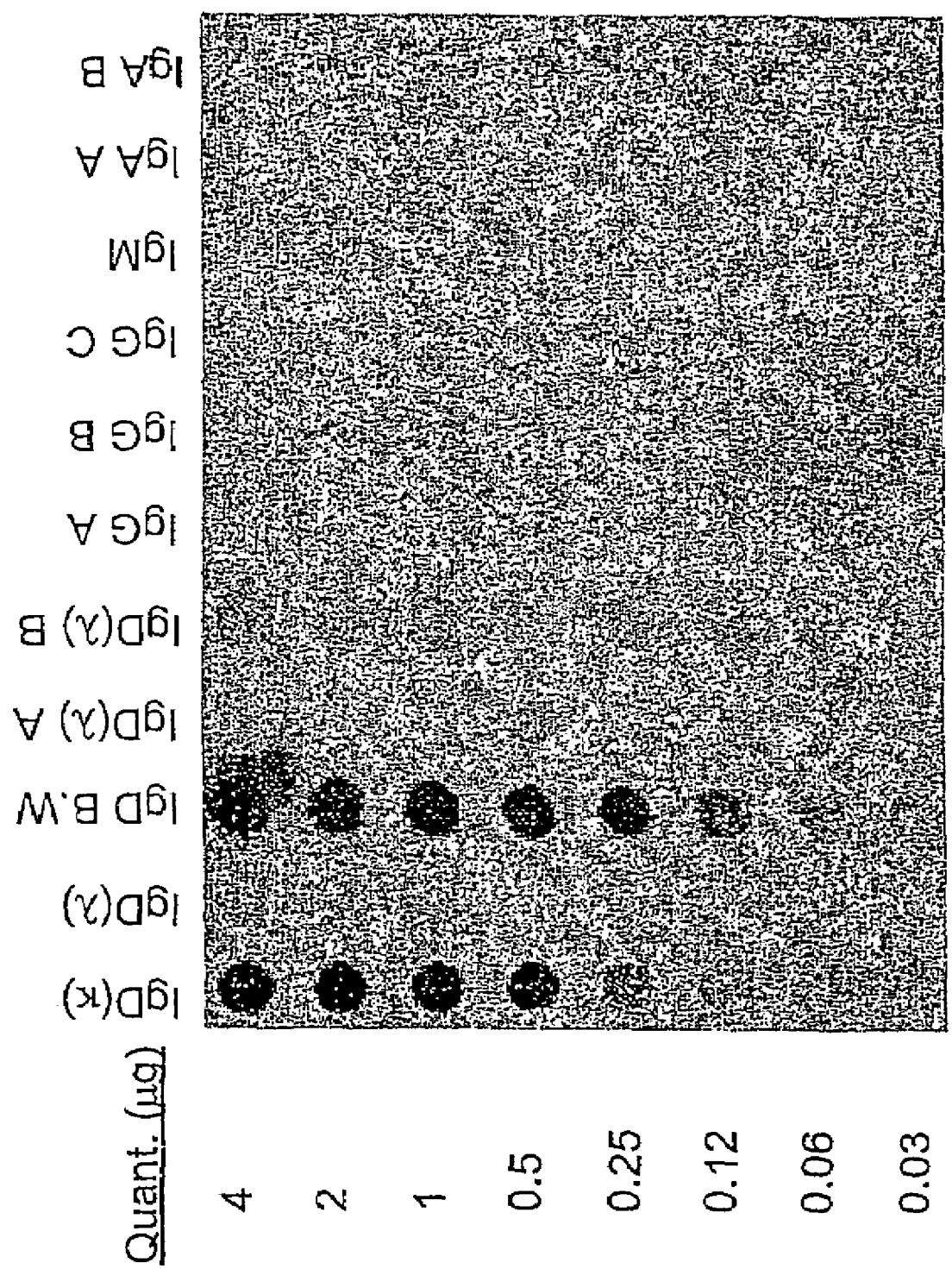
FIG. 3. Binding of MID to human myeloma sera representing different immunoglobulin classes. All sera were diluted in two-fold steps (4 to 0.3 μg) and applied to a nitrocellulose membrane. After saturation, washing and blocking, an [$^{125}$I]-MID-labeled probe was added. After overnight incubation and additional washings, specific MID-IgD binding was visualized by autoradiography.
Figure 4:
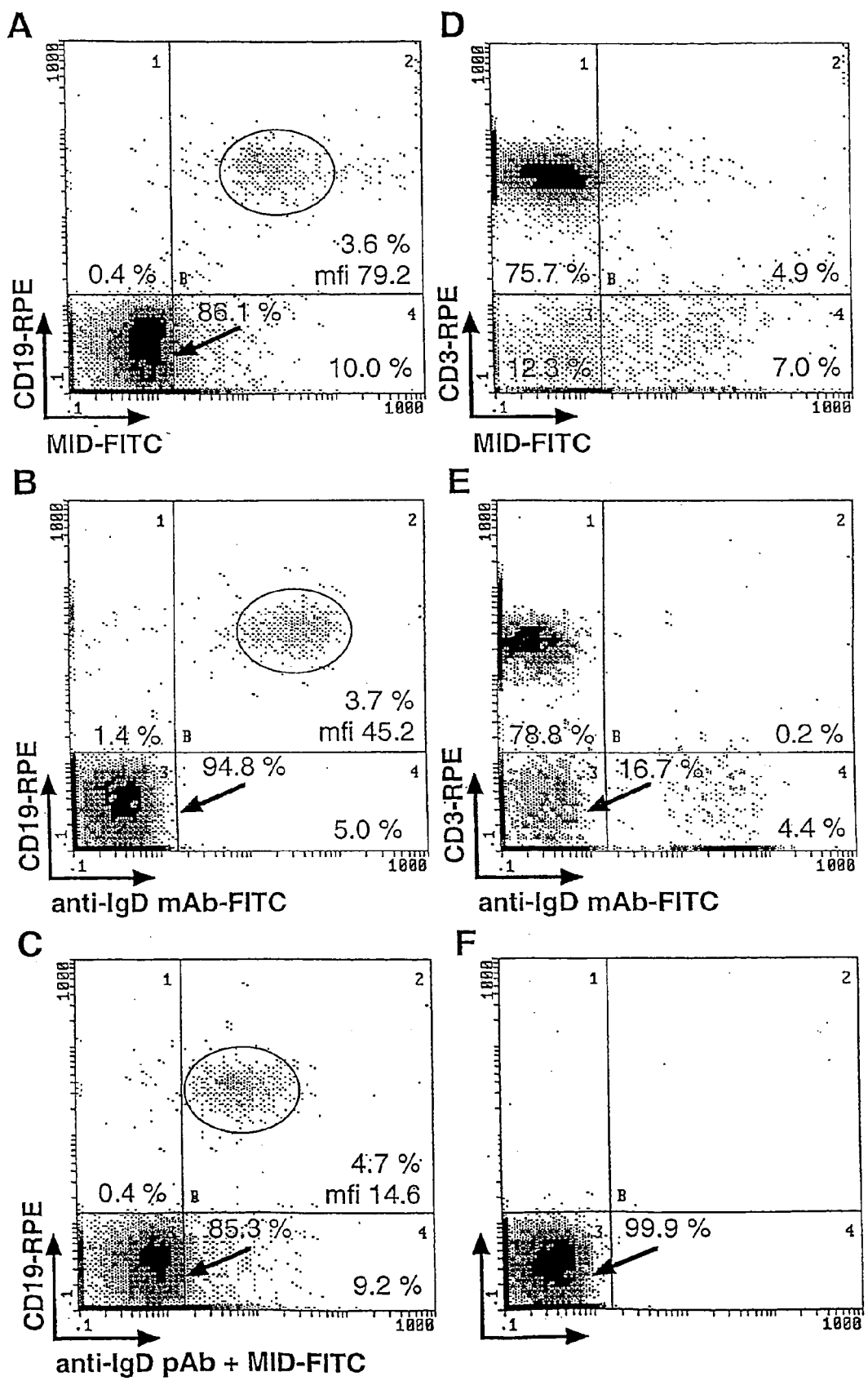
FIG. 4. IgD-bearing B cells specifically bound FITC-conjugated MID. PBLs stained with RPE-conjugated mAbs against CD19+ (A) or CD3+ (D) followed by incubation with MID-FITC were compared to PBLs incubated with anti-CD19 mAb in addition to an anti-IgD mAb (B). Double staining with CD3+ and anti-IgD mAb is demonstrated in (E). In (C), a panel with PBLs pre-incubated with a rabbit immunoglobulin fraction against human IgD followed by addition of anti-CD19 mAb and MID-FITC is shown. A control sample with no antibodies or MID-FITC is also included (F).

Purified MID specifically attracted human soluble IgD as revealed in dot and Western blots (FIGS. 2 and 3, Table III). To test whether MID bound to the surface-expressed B cell receptor (BCR) IgD, human peripheral blood lymphocytes (PBLs) were isolated. FITC was conjugated to MID followed by incubation with PBLs for 45 min on ice. In parallel, PBLs were labeled with RPE-conjugated mAbs directed against the T cell marker CD3 or the B cell specific surface antigen CD19 and subsequently analysed by flow cytometry (FIG. 4). Interestingly, a large fraction of CD19$^+$ lymphocytes bound significant amounts of MID-FITC (FIG. 4A), whereas T cells (CD3$^+$ lymphocytes) only displayed a non-specific background binding (FIG. 4D). The MID-FITC signal corresponded well with CD19$^+$ cells incubated with anti-IgD mAbs revealing IgD-postive B cells (FIG. 4B). To further elucidate the specificity of MID-FITC binding to IgD bearing CD19+ lymphocytes, PBLs were preincubated with a rabbit anti-human IgD immunoglobulin fraction. After incubation and washings, MID-FITC binding was analysed by flow cytometry according to the standard procedure. The antiserum almost completely inhibited specific MID-FITC binding to the IgD BCR when compared to cells incubated with the pre-immune serum. Mean fluorescence intensity decreased from 79.2 to 14.6 arbitrary units. Similar results were obtained with goat immunoglobulins raised against IgD (not shown). Thus, IgD-expressing B cells promoted specific MID-FITC binding to the surface-expressed BCR IgD.

Cloning of the Gene Encoding MID and DNA Sequence Analysis

Degenerate primers were designed according to the obtained amino terminal sequences of four peptide fragments originating from MID (Table II) and were used in PCRs in all possible combinations. The specific primers 2982+ and 3692− (FIG. 5) were synthesized using the deduced sequence of a distinctive PCR product generated with the degenerate primer pair 2629+/3693−. A PCR reaction using the specific primers in combination with the degenerate ones (718+ and 5772−) resulted in totally 5054 bp of the gene coding for MID. Flanking sequences surrounding the core of the mid gene were obtained by inverse PCR (IPCR). IPCR on EcORV- and AsuI/AccI-digested $M.$ $catarrhalis$ genomic DNA with the primer-pairs 2982+/945− and 3668+/120−, respectively, provided the sequence for the start-codon area. In addition, IPCR on HincII-digested moraxella genomic DNA with the primer-pair 5898+/5511− generated the 3' sequence including the stop-codon. The complete nucleotide sequence of the gene encoding MID in $M.$ $catarrhalis$ Bc5 is shown in SEQ ID NO 2 and the resulting amino acid sequence is shown in SEQ ID NO 1. Two alternative open reading frames were revealed and are 20' indicated at amino acid positions 1 and 17, see FIG. 6). Consequently, the length of the mid gene product was either 2123 or 2139 amino acids. In addition to a putative ribosome-binding site (AAGG), −10 (TAATTA) and −35 (TTGAAT) consensus sequence boxes were identified. Furthermore, 62 bases downstream of the TAA stop-codon an inverted repeat was found with the potential of stem-loop formation that is necessary for transcriptional termination. To get an overview of the similarity and identity between diferent mid genes, the sequences of the five ORF MID proteins were analysed. For 4 strains, the degree of identity and similarity was ≧75.8% and ≧78.3%, respectively (FIG. 7). In contrast, slightly lower values, ≧65.3% and ≧71.2%, respectively, were obtained for the fifth isolate (RH4). Identity and similarity with UspA1 was 5.5-11.1% and 8.3-17.9%, respectively, and with UspA2 6.5-7.5% respectively 11.1-12.4%.

The Mid Gene Can Be Detected in All $M.$ $catarrhalis$ Strains

By PCR analyses, the mid-I gene was detected in all 118 $M.$ $catarrhalis$ strains, whereas the Moraxella (nesseria)-related controls were negative. In addition, the size of the mid-1 gene was confirmed using primers spanning the whole gene including the start and stop codons. Analysis of the deduced amino acid sequence of MID differs from UspA1, UspA2 and the protein described in U.S. Pat. No. 5,808,024

The open reading frame defined a protein with a calculated molecular mass of just below 220 kDa that readily corresponded to the empirical value of approximately 200 kDa found by SDS-PAGE. The N-terminal amino acid sequence showed the typical characteristics of a signal peptide with a potential cleavage site between amino acids 66 and 67. Despite that the first amino acid after the signal peptidase cleavage site most likely was a glutamine residue, any sequence could not be determined by Edman degradation. Furthermore, no amino acid sequence was obtained after pyroglutamate aminopeptidase treatment. The predicted amino acid sequence was also subjected to a hydrophobicity profile analysis by the method of Kyte and Doolittle and showed mainly hydrophilic properties except for the putative signal peptide that was strongly hydrophobic. The deduced amino acid sequence for MID differs significantly from those for the protein described in U.S. Pat. No. 5,808,024 and also from the UspA-proteins (FIGS. 7 and 8).

The mid gene is distributed in all $M.$ $catarrhalis$ strains To investigate whether or not the mid gene existed in all $M.$ $catarrhalis$ strains, primers were chosen based upon a conserved area upstream of the open reading frame (ORF) and a conserved area downstream including the stop codon sequence (Forsgren et al., 2001). The mid gene was detected in all 86 clinical isolates and 7 type strains analysed, and the length of the genomic mid DNA was approximately 6,000 base pairs. The existance was further verified by Southern blots using a probe containing a sequence selected from the 3'-end of the gene. Southern blot experiments revealed that the moraxella strains contained only one mid gene.

Expression of Recombinant MID in $E.$ $Coli$

To confirm that the cloned mid gene corresponded to the purified IgD-binding protein, the gene including the predicted signal sequence and start codon was subcloned into the expression vector pET16(b) and thereby under the control of a T7 promoter. The resulting pET16-MID was subsequently transformed into $E.$ $coli$ BL21DE3 followed by induction with IPTG. Bacterial cells were lysed and subfractionated, and recombinant MID was localized by Western blots using human IgD as a probe. Important verifying characteristics of MID were provided from the expression experiments (FIG. 9). Firstly, following induction, cells containing pET16-MID were able to produce recombinant MID confirming the correct reading frame of the gene. Secondly, recombinant MID (as shown by SDS-PAGE) displayed a molecular mass of approximately 200 kDa, corresponding to the 217 kDa calculated value from the amino acid sequence. Thirdly, the recombinant protein was indeed the mid gene product in $E.$ $coli$ as its IgD-binding phenotype was confirmed by Western blot analysis. Total protein from $E.$ $coli$ containing induced pET16(b) vector without insert did not display any IgD-binding capacity (data not shown). Fourthly, the subcellular localization of the recombinant protein showed that MID was equally located in the cytoplasmic and the membrane fractions, but not in the periplasmic space. The localization of MID's in the membrane fraction correlated very well with the known outer membrane localization in $M.$ $catarrhalis$. IgD-binding is preserved in 238 amino acids of MID To in detail determine the MID IgD-binding region, 9 sequences derived from the full length MID were cloned into pET26b(+) and expressed in $E.$ $coli$. The recombinant proteins covered the entire MID sequence and their individual lengths and positions were as demonstrated in FIG. 10. The recombinant proteins comprising amino acid residues 69-1111 or 1011-2139 of MID did not bind IgD as revealed in Western and dot blots. In contrast, the protein MID902-1200 (protein fragment F1) attracted IgD-, strongly suggesting that the single IgD-binding region of MID was within that particular sequence.

To pinpoint the sequence responsible for the IgD-binding, the truncated MID902-1200 was systematically shortened at the N- and C-terminal ends (FIG. 11). Equimolar concentrations of the various recombinant proteins were compared to native full length MID1-2139 isolated from *M. catarrhalis*. The different recombinant proteins were diluted in four-fold steps, added to membranes and incubated with human IgD. On a molar basis, an essentially preserved IgD-binding capacity was detected for the truncated MID protein stretching from amino acid residue 962 to 1200. The shortest truncated protein still interacting with IgD-was localized between MID985 and MID1142 (fragment F6). The IgD-binding property was lost when the N-terminus was reduced to the MID1000 residue (fragment F4) or when the C-terminal was shortened to MID1130 (fragment F7). Finally, a fragment (MID902-1130; F8) with a longer N-terminal and a shorter C-terminal (compared to MID985-1200; F3) was also manufactured and analysed. However, this truncated MID did not interact with IgD, suggesting that the binding capacity was depending on a longer-C-terminal.

To further characterize the specific MID-dependent IgD-binding, an IgD ELISA was constructed using human IgD as bate. All the recombinant truncated MID fragments were subjected to ELISA followed by incubation with a specific rabbit anti-serum directed against MID902-1200. The ELISA was developed using HRP-conjugated goat anti-rabbit polyclonal antibodies. The same pattern as with the dot blot (FIG. 11) was observed, i.e. fragments F4, F7, and F8 was not attracted to the solid phase IgD, whereas the other fragments bound to a variable degree compared to full length MID (not shown).

Optimal M1D962-1200—IgD Interaction is Depending on a Tetramer Structure

To shed light upon the need for a tetramer structure in order to obtain an optimal IgD-binding, MID962-1200 (F2, SEQ ID NO 10) was incubated at 60 or 100° C. followed by analysis on SDS-PAGE and Western blots. MID962-1200 formed both a monomer and a tetramer after pre-treatment at 60° C. (FIG. 12A). The tetrameric structure was, however, disrupted at 100° C. and resulted in a monomeric form, which displayed a considerably weaker binding to IgD when examined in Western blots (FIGS. 12A and B). To investigate the capability of the tetramer to bind IgD in comparison with the monomeric form, the MID962-1200 fragment, SEQ ID NO 10, was subjected to analysis at 60° C. in 6 different experiments. The heat treated protein was subjected to SDS-PAGE and the IgD-binding activity was analysed by Western blots. Resulting gels and filters were analysed by densitometry and the protein concentration (density) of the monomer was divided with the corresponding tetramer concentration. The obtained value (%) was related to the concentration (μg) of total protein loaded on the gels. Interestingly, when IgD-binding to the tetrameric respectively monomeric forms were compared, a 23-fold more efficient binding to IgD was found with the tetrameric MID962-1200 (FIG. 12C). *M. catarrhalis* IgD-binding protein (MID) hemagglutinates human erythrocytes To investigate a putative involvement of MID in hemagglutination, a series of clinical isolates that either expressed MID or by phase variation had shut off the mid gene was selected. Interestingly, all out of 21 isolates expressing MID hemagglutinated human erythrocytes, whereas only four out of the MID-negative strains (n=21) hemagglutinated the red blood cells. An almost full correlation between hemagglutinating capacity and MID expression was observed. UspA1/2 expression was similar and irrespective of the MID expression.

These initial experiments prompted us to examine whether or not purified MID protein from the model strain *M. catarrhalis* Bc5 (Forsgren et al., 2001) hemagglutinates erythrocytes. To mimic the bacterial surface, MID was conjugated to Sepharose beads and incubated with the human erythrocytes. Bovine serum albumin (BSA) linked to Sepharose was included as a negative control. Interestingly, the human erythrocytes were hemagglutinated in the presence of MID-Sepharose, whereas BSA-Sepharose did not interfere with the erythrocytes (data not shown). The hemagglutinating domain of MID is located between amino acid residues Alanine764 and Serine913

To dissect the molecule and pin-point the specific site of the molecule that was responsible for the hemagglutination, a series of truncated DNA fragments of the mid gene was cloned and recombinantly expressed in *E. coli* (FIG. 10). Polyclonal antibodies against the truncated MID proteins were raised in rabbits and used in an ELISA. In preparatory experiments, antibodies to MID and the MID-derived proteins were titrated to give similar values when tested in ELISA against respective antigens. The capacity of the truncated MID proteins to bind to lysed erythrocytes was then measured in ELISA using the specific antibodies at appropriate concentrations. MID or MID764-913 (fragment E) gave higher ELISA values (4 to 16 times) as compared to the other truncated MID proteins. Thus, the hemagglutinating structure of MID seemed to be located within amino acid residues 764-913 of MID (SEQ ID NO 8).

MID764-913 (Fragment E, SEQ ID NO 8) Binds Directly to Both Eryhtrocytes and Type II Alveolar Epithelial Cells To further confirm the importance of MID764-913 as an adhesin, MID and a selection of the truncated MID-derived proteins were radiolabelled and tested in direct binding experiments with human erythrocytes and alveolar epithelial cells (FIG. 13). Both [125I]-MID and [125I]-MID764-913 strongly bound to erythrocytes, whereas the truncated MID fragments MID367-590 (fragment C), MID902-1200 (F), MID1011-1446 (G), and MID1616-2139 (I) did not bind above background levels (FIG. 13A). In parallel, the alveolar epithelial cell line A549 also attracted both the full length [$^{125}$I]-labelled MID and the truncated MID764-913 (FIG. 13B). All the other fragments did not bind to the epithelial cells. Taken together, the fragment MID764-913 (SEQ ID NO 8) was the crucial part of the adhesin MID that mediated the attachment to mammalian cells.

Antibodies to Full Length MID1-2139 and M1D764-913 Inhibit Adherence of *M. catarrhalis* to Type II Alveolar Epithelial Cells To further analyse the influence of full length MID and MID764-963 on *M. catarrhalis* adherence to type II alveolar epithelial cells, a MID-expressing and a MID-deficient *M. catarrhalis* strain were preincubated with antibodies to MID and subsequently added to alveolar epithelial cells for adherence. As demonstrated in FIG. 14, polyclonal antibodies directed against full length MID1-2139 and MID763-913 (fragment E, SEQ ID NO 8) effectively inhibited adherence for the MID-expressing isolate. In contrast, pre-immune serum and a pAb directed against MID1011-1466 (fragment G) did not significantly interfere with adhesion.

REFERENCES

1. Forsgren, A. and Grubb, A. (1979) Many bacterial species bind human IgD. J. Immunol. 122, 1468-1472.
2. Banck, G. and Forsgren, A. (1978) Many bacterial species are mitogenic for human blood lymphocytes. Scand. J. Immunol. 8, 347-354.

3. Calvert, J. E. and Calogeres, A. (1986) Characteristics of human B cells responsive to the T-independent mitogen *Branhamella catarrhalis*. Immunology 58, 37-41.
4. Forsgren, A., Penta, A., Schlossman, S. F. and Tedder, T. F. (1988) *Branhamella catarrhalis* activates human B lymphocytes following interactions with surface IgD and class I major histocompatibility complex antigens. Cell. Immunol. 112, 78-88.
5. Janson, H., Carlén, B., Cervin, A., Forsgren, A., Björk-Magnusdottir, A., Lindberg, S. and Runer, T. (1999) Effects on the ciliated epithelium of protein D-producing and -nonproducing nontypeable *Haemophilus influenzae* in nasopharyngeal tissue cultures. J. Infect. Dis. 180, 737-746.
6. Sasaki, K. and Munson Jr., R. S. (1993) Protein D of *Haemophilus influenzae* is not a universal immunoglobulin D-binding protein. Infect. Immun. 61, 3026-3031.
7. Helminen, M. E., Beach, R., Maciver, I., Jarosik, G., Hansen, E. J. and Leinonen, M. (1995) Human immune response against outer membrane proteins of *Moraxella (Branhamella) catarrhalis* determined by immunoblotting and enzyme immunoassay. Clin. Diagn. Lab. Immunol. 2, 35-39.
8. Aebi, C., Maciver, I., Latimer, J. L., Cope, L. D., Stevens, M. K., Thomas, S. E., McCracken, G. H. and Hansen, E. J. (1997) A protective epitope of *Moraxella catarrhalis* is encoded by two different genes. Infect. Immun. 65, 4367-4377.
9. Cope, L. D., Lafontaine, E. R., Slaughter, C. A., Hasemann, C. A. Jr., Aebi, C., Henderson, F. W., McCracken, G. H. Jr and Hansen, E. J. (1999) Characterization of *Moraxella catarrhalis* uspA1 and uspA2 genes and their encoded products. J Bacteriol 181, 4026-4034.
10. Klingman, K. L. and Murphy, T. F. (1994) Purification and characterization of a high-molecular-weight outer membrane protein of *Moraxella(Branhamella) catarrhalis*. Infect. Immun. 62, 1150-1155.
11. WO 98/28333
12. Sasaki, K., Harkness, R. E., Loosmoore, S. M. and Klein, M. H. (1998) U.S. Pat. No. 5,808,024.
13. Fitzgerald, M., Mulcahy, R., Murphy, S., Keane, C., Coakley, D. and Scott, T. (1997) A 200 kDa protein is associated with haemagglutinating isolates of *Moraxella (Branhamella) catarrhalis*. FEMS Immun. Med. Microbiol. 18, 209-216.
14. Tucker, K., Plosila, L., and Samuel, J. (1994) Correlation between hemagglutination and globotetraosyl-ceramide binding by *Branhamella catarrhalis*. Abstract 117 of the 94th General meeting of the American Society for Microbiology.
15. Lunde E, Munthe LA, Vabo A, Sandlie I, Bogen B. (1999) Antibodies engineered with IgD specificity efficiently deliver integrated, T-cell epitopes for antigen presentation by B cells. Nat Biotechnol. 17, 670-675.
16. Lycke N. (2001) The B-cell targeted CTA1-DD vaccine adjuvant is highly effective at enhancing anti-body as well as CTL responses. Curr. Opin. Mol. Ther. 3, 37-44.
17. Ito O, Harada M, Takenoyama M, Tamada K, Li T, Abe K, Fujie H, Nomoto K. 1998 Vaccination with activated B cells pulsed with tumor-lysates can induce tumor-specific CD4+ T cells in vivo. Immunobiol. 199, 133-147.

The invention claimed is:

1. An isolated surface exposed protein comprising an amino acid sequence as described in SEQ ID NO: 1, wherein said isolated surface exposed protein can be detected in *Moraxella catarrhalis*, has an apparent molecular weight of 200 kDa, and selectively binds membrane bound or soluble IgD.

2. An isolated immunogenic and adhesive fragment of a surface exposed protein, wherein said isolated immunogenic and adhesive fragment of a surface exposed protein comprises an amino acid sequence as described in SEQ ID NO: 8, and binds to erythrocytes and epithelial cells.

3. An isolated fusion protein or polypeptide, comprising the isolated surface exposed protein of claim 1 combined with another protein.

* * * * *

UNITED STATES PATENT AND TRADEMARK OFFICE
CERTIFICATE OF CORRECTION

PATENT NO. : 7,470,432 B2 Page 1 of 1
APPLICATION NO. : 10/480456
DATED : December 30, 2008
INVENTOR(S) : Forsgren et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this

Twenty-first Day of September, 2010

David J. Kappos
*Director of the United States Patent and Trademark Office*

SEQUENCE LISTING

```
<160> NUMBER OF SEQ ID NOS: 11

<210> SEQ ID NO 1
<211> LENGTH: 2139
<212> TYPE: PRT
<213> ORGANISM: Moraxella catarrhalis

<400> SEQUENCE: 1

Met Asn His Ile Tyr Lys Val Ile Phe Asn Lys Ala Thr Gly Thr Phe
 1               5                  10                  15

Met Ala Val Ala Glu Tyr Ala Lys Ser His Ser Thr Gly Gly Ser Cys
             20                  25                  30

Ala Thr Gly Gln Val Gly Ser Val Cys Thr Leu Ser Phe Ala Arg Val
         35                  40                  45

Ala Ala Leu Ala Val Leu Val Ile Gly Ala Thr Leu Asn Gly Ser Ala
     50                  55                  60

Tyr Ala Gln Gln Asp Pro Arg His Ile Ala Ile Asp Gly Asn Ser Ser
 65                  70                  75                  80

Asn Thr Ser Ser Gly Thr Ala Arg Ala Thr Gly Asp Arg Ala Ile Ala
                 85                  90                  95

Leu Gly Glu Asn Ala Asn Ala Glu Gly Gly Gln Ala Ile Ala Ile Gly
            100                 105                 110

Ser Ser Asn Lys Thr Gly Gly Arg Asn Ala Leu Asn Ile Gly Thr Asp
        115                 120                 125

Ala Lys Gly Glu Glu Ser Ile Ala Ile Gly Gly Asp Val Val Ala Glu
    130                 135                 140
```

```
Gly Thr Ala Ser Ile Ala Ile Gly Gly Asp Asp Leu His Leu Trp Asp
145                 150                 155                 160

Glu Pro Asn Lys Gln Lys Phe Leu Asp Pro Lys Val Lys Glu Leu Ile
                165                 170                 175

Leu Lys His Gln Glu Leu Asn Asn Ile Tyr Lys Leu Pro Asp Gly Ser
            180                 185                 190

Pro Gln Arg Tyr Phe Arg Thr Tyr Ala Lys Gly His Ala Ser Ile Ala
        195                 200                 205

Leu Gly Thr Met Thr Gln Ala Glu Gly His Phe Ala Asn Ala Phe Gly
    210                 215                 220

Thr Arg Ala Thr Ala Lys Gly Asn Tyr Ser Leu Ala Val Gly Leu Thr
225                 230                 235                 240

Ala Gln Ala Asn Thr Glu Ser Ser Ile Ala Val Gly Ser Asn Ala Gln
                245                 250                 255

Ala Asn Gly Phe Ala Ala Thr Ala Ile Gly Gly Thr Lys Ala Asp
            260                 265                 270

Leu Gly Arg Ser Ile Ala Leu Gly Phe Gly Ser Gln Ile Leu Thr Lys
        275                 280                 285

Glu Lys Asp Ser His Asn Asn Thr Asn Val Tyr Val Pro Gln Gly Glu
    290                 295                 300

Ile Leu Glu Glu Arg Tyr Lys Ala Thr Glu Asn Gly Gln Ser Pro Asn
305                 310                 315                 320

Lys Val Val Asp Ile Phe Ser Ile Gly Ser Ser Ile Lys Arg Lys
                325                 330                 335

Ile Ile Asn Val Gly Ala Gly Ser Gln Glu Thr Asp Ala Val Asn Val
            340                 345                 350

Ala Gln Leu Lys Leu Val Glu Arg Val Ala Lys Arg Gln Ile Thr Phe
        355                 360                 365

Gln Gly Asp Asp Ser Asn Asn Ser Val Lys Lys Gly Leu Gly Gln Thr
    370                 375                 380

Leu Thr Ile Lys Gly Gly Lys Thr Glu Thr Gly Glu Leu Thr Glu Asn
385                 390                 395                 400

Asn Ile Gly Val Val Gln Asp Asp Asn Gly Asn Gly Leu Lys Val Lys
                405                 410                 415

Leu Ala Lys Asp Leu Thr Gly Leu Thr Lys Val Ala Val Asn Gly Asn
            420                 425                 430

Gly Ala Asn Asn Ala Glu Leu Leu Asn Gly Gly Leu Thr Phe Ser Thr
        435                 440                 445

Ser Gly Ala Asn Ala Gly Lys Thr Val Tyr Gly Thr Asp Gly Val Lys
    450                 455                 460

Phe Thr Asn Asn Thr Gly Thr Gly Thr Gly Thr Ala Ile Pro Asp Thr
465                 470                 475                 480

Thr Arg Ile Thr Lys Asn Lys Ile Gly Phe Ala Gly Ala Asp Glu Gln
                485                 490                 495

Val Asp Glu Ser Lys Pro Tyr Leu Asp Asn Glu Lys Leu Lys Val Gly
            500                 505                 510

Thr Val Glu Ile Lys Lys Thr Gly Ile Asn Ala Gly Asn Gln Glu Ile
        515                 520                 525

Thr Lys Val Lys Ser Ala Ile Val Asp Ala Val Asn Gly Gln Ala Asn
    530                 535                 540

Gln Ser Phe Val Asn Leu Leu Glu Thr Ala Gly Thr Asn Thr Asn Lys
545                 550                 555                 560

Gln Asn Ser Ala Ala Thr Val Lys Asp Leu Tyr Asp Leu Ser Gln Ser
```

-continued

```
                565                 570                 575
Pro Leu Thr Phe Thr Gly Asp Ser Gly Asn Val Lys Arg Lys Leu Gly
                580                 585                 590
Gln Thr Leu Thr Ile Thr Gly Gly Gln Thr Lys Thr Asp Gln Leu Thr
                595                 600                 605
Asp Asn Asn Ile Gly Val Val Ala Gly Thr Asn Gly Leu Thr Val Lys
                610                 615                 620
Leu Ala Lys Thr Leu Asn Ser Leu Thr Glu Val Asn Thr Ala Thr Leu
625                 630                 635                 640
Asn Ala Thr Asn Lys Val Lys Val Asp Asn Ser Thr Gly Asn Thr Ala
                645                 650                 655
Glu Leu Leu Asn Asn Gly Leu Thr Phe Thr Gln Thr Thr Gly Ala Asn
                660                 665                 670
Ser Gly Lys Thr Val Tyr Gly Asn Asp Gly Leu Lys Phe Thr Asn Ser
                675                 680                 685
Ala Asn Lys Ala Leu Gly Gly Thr Thr Tyr Ile Thr Lys Asp Gln Val
                690                 695                 700
Gly Phe Ser Asn Gln Asp Gly Leu Leu Asp Glu Ser Lys Pro Tyr Leu
705                 710                 715                 720
Asn Arg Glu Lys Leu Lys Val Gly Lys Ile Glu Ile Lys Asp Ser Gly
                725                 730                 735
Ile Asn Ala Gly Gly Lys Ala Ile Thr Gly Leu Pro Ser Thr Leu Pro
                740                 745                 750
Asn Thr Thr Tyr Thr Ala Pro Gly Val His Thr Ala Leu His Gly Ser
                755                 760                 765
Thr Ile Ser Asn Asp Asp Lys Thr Arg Ala Ala Ser Ile Ala Asp Val
                770                 775                 780
Leu Asn Ala Gly Phe Asn Leu Glu Gly Asn Gly Glu Ala Val Asp Phe
785                 790                 795                 800
Val Ser Thr Tyr Asp Thr Val Asn Phe Ala Asp Gly Asn Ala Thr Thr
                805                 810                 815
Ala Lys Val Thr Tyr Asp Asn Lys Thr Ser Lys Val Ala Tyr Asp Val
                820                 825                 830
Asn Val Asp Gly Thr Thr Ile His Leu Thr Gly Thr Asn Gly Lys Lys
                835                 840                 845
Asn Gln Ile Gly Val Lys Thr Thr Leu Thr Thr Lys Arg Ala Lys
850                 855                 860
Gly Asn Thr Ala Thr Asn Phe Ser Val Asn Ser Gly Asp Asp Asn Ala
865                 870                 875                 880
Leu Ile Asn Ala Lys Asp Ile Ala Asp Asn Leu Asn Thr Leu Ala Gly
                885                 890                 895
Glu Ile Arg Thr Ala Lys Gly Thr Ala Ser Thr Ala Leu Gln Thr Phe
                900                 905                 910
Ser Ile Ile Asp Glu Gln Gly Asn Asn Phe Met Val Gly Asn Leu Tyr
                915                 920                 925
Ser Gly Tyr Asp Thr Ser Asn Thr Ser Glu Thr Val Thr Phe Val Gly
                930                 935                 940
Glu Asn Gly Ile Thr Thr Lys Val Asn Lys Gly Lys Val Lys Val Gly
945                 950                 955                 960
Ile Asp Gln Thr Lys Gly Leu Thr Thr Pro Lys Leu Thr Val Gly Ser
                965                 970                 975
Ser Asn Gly Lys Gly Ile Val Ile Asp Ser Lys Asp Gly Gln Asn Thr
                980                 985                 990
```

```
Ile Thr Gly Leu Ser Asn Thr Leu Thr Asp Ala Thr Asn Ala Thr Thr
        995                 1000                1005

Gly His Val Ser Glu Ile Gln Gly Leu Ala Gln Gly Ala Asn Lys Thr
    1010                1015                1020

Arg Ala Ala Ser Ile Gly Asp Val Leu Asn Ala Gly Phe Asn Leu Gln
1025                1030                1035                1040

Gly Asn Gly Glu Ala Lys Asp Phe Val Ser Thr Tyr Asp Thr Val Asn
            1045                1050                1055

Phe Ile Asp Gly Asn Ala Thr Thr Ala Lys Val Thr Tyr Asp Asp Thr
                1060                1065                1070

Lys Gln Thr Ser Thr Val Thr Tyr Asp Val Asn Val Asp Asn Lys Thr
        1075                1080                1085

Leu Glu Val Thr Gly Asp Lys Lys Leu Gly Val Lys Thr Thr Thr Leu
    1090                1095                1100

Thr Lys Thr Ser Ala Asn Gly Asn Ala Thr Lys Phe Ser Ala Ala Asp
1105                1110                1115                1120

Gly Asp Ala Leu Val Lys Ala Ser Asp Ile Ala Thr His Leu Asn Thr
            1125                1130                1135

Leu Ala Gly Asp Ile Gln Thr Ala Lys Gly Ala Ser Gln Ala Ser Ser
                1140                1145                1150

Ser Ala Ser Tyr Val Asp Ala Asp Gly Asn Lys Val Ile Tyr Asp Ser
        1155                1160                1165

Thr Asp Lys Lys Tyr Tyr Gln Ala Lys Asn Asp Gly Thr Val Asp Lys
    1170                1175                1180

Thr Lys Glu Val Ala Lys Asp Lys Leu Val Ala Gln Ala Gln Thr Pro
1185                1190                1195                1200

Asp Gly Thr Leu Ala Arg Met Asn Val Lys Ser Val Ile Asn Lys Glu
            1205                1210                1215

Gln Val Asn Asp Ala Asn Lys Lys Gln Gly Ile Asn Glu Asp Asn Ala
        1220                1225                1230

Phe Val Lys Gly Leu Glu Lys Ala Ala Ser Asp Asn Lys Thr Lys Asn
    1235                1240                1245

Ala Ala Val Thr Val Gly Asp Leu Asn Ala Val Ala Gln Thr Pro Leu
1250                1255                1260

Thr Phe Ala Gly Asp Thr Gly Thr Thr Ala Lys Lys Leu Gly Glu Thr
1265                1270                1275                1280

Leu Thr Ile Lys Gly Gly Gln Thr Asp Thr Asn Lys Leu Thr Asp Asn
        1285                1290                1295

Asn Ile Gly Val Val Ala Gly Thr Asp Gly Phe Thr Val Lys Leu Ala
            1300                1305                1310

Lys Asp Leu Thr Asn Leu Asn Ser Val Asn Ala Gly Thr Lys Ile
        1315                1320                1325

Asp Asp Lys Gly Val Ser Phe Val Asp Ala Asn Gly Gln Ala Lys Ala
    1330                1335                1340

Asn Thr Pro Val Leu Ser Ala Asn Gly Leu Asp Leu Gly Gly Lys Arg
1345                1350                1355                1360

Ile Ser Asn Ile Gly Ala Ala Val Asp Asp Asn Asp Ala Val Asn Phe
            1365                1370                1375

Lys Gln Phe Asn Glu Val Ala Lys Thr Val Asn Leu Asn Asn Gln
        1380                1385                1390

Ser Asn Ser Gly Ala Ser Leu Pro Phe Val Val Thr Asp Ala Asn Gly
    1395                1400                1405
```

```
Lys Pro Ile Asn Gly Thr Asp Asp Lys Pro Gln Lys Ala Ile Lys Gly
    1410                1415                1420

Ala Asp Gly Lys Tyr Tyr His Ala Asn Ala Asn Gly Val Pro Val Asp
1425                1430                1435                1440

Lys Asp Gly Asn Pro Ile Thr Asp Ala Asp Lys Leu Ala Asn Leu Ala
                1445                1450                1455

Ala His Gly Lys Pro Leu Asp Ala Gly His Gln Val Val Ala Ser Leu
            1460                1465                1470

Gly Gly Asn Ser Asp Ala Ile Thr Leu Thr Asn Ile Lys Ser Thr Leu
        1475                1480                1485

Pro Gln Ile Asp Thr Pro Asn Thr Gly Asn Ala Asn Ala Gly Gln Ala
    1490                1495                1500

Gln Ser Leu Pro Ser Leu Ser Ala Ala Gln Gln Ser Asn Ala Ala Ser
1505                1510                1515                1520

Val Lys Asp Val Leu Asn Val Gly Phe Asn Leu Gln Thr Asn His Asn
                1525                1530                1535

Gln Val Asp Phe Val Lys Ala Tyr Asp Thr Val Asn Phe Val Asn Gly
            1540                1545                1550

Thr Gly Ala Asp Ile Thr Ser Val Arg Ser Ala Asp Gly Thr Met Ser
        1555                1560                1565

Asn Ile Thr Val Asn Thr Ala Leu Ala Ala Thr Asp Asp Gly Asn
    1570                1575                1580

Val Leu Ile Lys Ala Lys Asp Gly Lys Phe Lys Ala Asp Asp Leu
1585                1590                1595                1600

Met Pro Asn Gly Ser Leu Lys Ala Gly Lys Ser Ala Ser Asp Ala Lys
                1605                1610                1615

Thr Pro Thr Gly Leu Ser Leu Val Asn Pro Asn Ala Gly Lys Gly Ser
            1620                1625                1630

Thr Gly Asp Ala Val Ala Leu Asn Asn Leu Ser Lys Ala Val Phe Lys
        1635                1640                1645

Ser Lys Asp Gly Thr Thr Thr Thr Val Ser Ser Asp Gly Ile Ser
    1650                1655                1660

Ile Gln Gly Lys Asp Asn Ser Asn Ile Thr Leu Ser Lys Asp Gly Leu
1665                1670                1675                1680

Asn Val Gly Gly Lys Val Ile Ser Asn Val Gly Lys Gly Thr Lys Asp
                1685                1690                1695

Thr Asp Ala Ala Asn Val Gln Gln Leu Asn Arg Ser Thr Gln Leu Val
            1700                1705                1710

Gly Ser Trp Val Met Ala Gly Asn Asp Asn Ala Asp Gly Asn Gln Val
        1715                1720                1725

Asn Ile Ala Asp Ile Lys Lys Asp Pro Asn Ser Gly Ser Ser Ser Asn
    1730                1735                1740

Arg Thr Val Ile Lys Ala Gly Thr Val Leu Gly Gly Lys Gly Asn Asn
1745                1750                1755                1760

Asp Thr Glu Lys Leu Ala Thr Gly Gly Val Gln Val Gly Val Asp Lys
                1765                1770                1775

Asp Gly Asn Ala Asn Gly Asp Leu Ser Asn Val Trp Val Lys Thr Gln
            1780                1785                1790

Lys Asp Gly Ser Lys Lys Ala Leu Leu Ala Thr Tyr Asn Ala Ala Gly
        1795                1800                1805

Gln Thr Asn Tyr Leu Thr Asn Asn Pro Ala Glu Ala Ile Asp Arg Ile
    1810                1815                1820

Asn Glu Gln Gly Ile Arg Phe Phe His Val Asn Asp Gly Asn Gln Glu
```

-continued

```
1825                1830                1835                1840

Pro Val Val Gln Gly Arg Asn Gly Ile Asp Ser Ser Ala Ser Gly Lys
                1845                1850                1855

His Ser Val Ala Val Gly Tyr Lys Ala Lys Ala Asp Gly Glu Ala Ala
            1860                1865                1870

Val Ala Ile Gly Arg Gln Thr Gln Ala Gly Asn Gln Ser Ile Ala Ile
        1875                1880                1885

Gly Asp Asn Ala Gln Ala Thr Gly Asp Gln Ser Ile Ala Ile Gly Thr
    1890                1895                1900
Gly Asn Val Val Ala Gly Lys His Ser Gly Ala Ile Gly Asp Pro Ser
1905                1910                1915                1920

Thr Val Lys Ala Asp Asn Ser Tyr Ser Val Gly Asn Asn Asn Gln Phe
                1925                1930                1935

Thr Asp Ala Thr Gln Thr Asp Val Phe Gly Val Gly Asn Asn Ile Thr
            1940                1945                1950
Val Thr Glu Ser Asn Ser Val Ala Leu Gly Ser Asn Ser Ala Ile Ser
        1955                1960                1965
Ala Gly Thr His Ala Gly Thr Gln Ala Lys Lys Ser Asp Gly Thr Ala
    1970                1975                1980
Gly Thr Thr Thr Thr Ala Gly Ala Thr Gly Thr Val Lys Gly Phe Ala
1985                1990                1995                2000

Gly Gln Thr Ala Val Gly Ala Val Ser Val Gly Ala Ser Gly Ala Glu
                2005                2010                2015

Arg Arg Ile Gln Asn Val Ala Ala Gly Glu Val Ser Ala Thr Ser Thr
            2020                2025                2030

Asp Ala Val Asn Gly Ser Gln Leu Tyr Lys Ala Thr Gln Ser Ile Ala
        2035                2040                2045
Asn Ala Thr Asn Glu Leu Asp His Arg Ile His Gln Asn Glu Asn Lys
    2050                2055                2060
Ala Asn Ala Gly Ile Ser Ser Ala Met Ala Met Ala Ser Met Pro Gln
2065                2070                2075                2080
Ala Tyr Ile Pro Gly Arg Ser Met Val Thr Gly Gly Ile Ala Thr His
                2085                2090                2095

Asn Gly Gln Gly Ala Val Ala Val Gly Leu Ser Lys Leu Ser Asp Asn
            2100                2105                2110

Gly Gln Trp Val Phe Lys Ile Asn Gly Ser Ala Asp Thr Gln Gly His
        2115                2120                2125
Val Gly Ala Ala Val Gly Ala Gly Phe His Phe
    2130                2135

<210> SEQ ID NO 2
<211> LENGTH: 6889
<212> TYPE: DNA
<213> ORGANISM: Moraxella catarrhalis

<400> SEQUENCE: 2
aatcattacc ccccccttta tgggggatca tatgaataga atattatgat tgtatctgat      60
tattgtatca gaatggtgat gcctacgagt tgatttgggt gaatcactct attatttgat     120
atgttttgaa actaatctat tgacttaaat caccatatgg ttataattta gcataatggt     180 aggcttttttg taaaaatcac atcgcaatat tgttctactg ttactaccat gcttgaatga     240
cgatcccaat catcagattc attcaagtga tgtgtttgta tacgcatcat ttaccctaat     300
tatttcaatc gaaatgccta tgtcagcatg tatcattttt ttaaggtaaa ccaccatgaa     360
```

-continued

```
tcacatctat aaagtcatct ttaacaaagc cacaggcaca tttatggccg tggcggaata    420
tgccaaatcc cacagcacgg ggggtagctg tgctacaggg caagttggca gtgtatgcac    480
tctgagcttt gcccgtgttg ccgcgctcgc tgtcctcgtg atcggtgcga cgctcaatgg    540
cagtgcttat gctcaacaag atcccagaca tatcgcaatt gatggcaaca gctcgaacac    600
atcctcaggc actgcccgtg cgacaggtga tcgagccatt gctcttggtg aaaatgctaa    660
tgcagagggc ggtcaagcca tcgccatcgg tagtagcaat aaaacaggtg gtagaaacgc    720
gctgaatata ggtaccgatg ccaaaggtga ggagtccatc gccatcggtg gtgatgtagt    780
ggctgagggt actgcctcga ttgccatcgg tggtgatgac ttacatttgt gggatgaacc    840
aaataagcaa aagttcctcg acccaaaagt taaagaattg attttaaaac atcaagaatt    900
aaacaacata tacaaactgc ctgatggtag tcctcaaaga tattttcgca catacgcaaa    960
gggacacgcc agtattgcac taggaaccat gacacaggca gagggtcatt ttgccaacgc   1020
ctttggtaca cggcaacag ctaaaggcaa ctattccttg gcagtgggtc ttaccgccca   1080
agccaacaca gaatcttcaa tcgctgttgg ttctaatgca caagctaacg ggtttgcagc   1140
gacagccatt ggtggaggta ctaaagctga tttgggtcga agcatagccc taggttttgg   1200
ttctcagatc cttactaagg agaaggatag tcataacaat accaatgtct atgtaccaca   1260
aggtgaaata ttagaagagc ggtataaagc caccgaaaac ggtcagtcgc ctaataaggt   1320
agtggatata ttttccattg gtagtagctc tatcaaacgt aaaatcatca atgtcggtgc   1380
gggttctcag gagaccgatg cggtcaatgt ggcacagctt aaattggtgg agcgggtggc   1440
taagcgtcaa attactttc agggtgatga tagcaataat agcgtaaaaa aaggtttggg   1500
tcagacttta actattaaag gtggtaaaac agagaccggt gaactaaccg aaaataacat   1560
cggtgtggta caagatgata atggtaatgg tctgaaagtt aaacttgcta agatctgac    1620
tggtttgacc aaggttgcag taatggtaa tggtgctaac aacgccgagc tactaaacgg   1680
tggtctgacc ttttcgacat caggtgccaa tgcaggcaaa acggtctatg gcactgatgg   1740
ggtgaagttt actaataata caggaacagg aacaggaacg gcaatacccg acactactcg   1800
tattaccaaa aataaaattg gctttgctgg ggctgatgaa caagttgatg aaagcaaacc   1860
ttatcttgac aacgaaaagc taaagttggc cacagttgag attaaaaaaa ctggcatcaa   1920
tgcaggtaat caagaaatta ccaaggtcaa atctgccatt gttgatgcag ttaatggaca   1980
agcaaatcaa agcttgtga accttctaga aacagcaggc acaaacacca acaaacaaaa   2040
ctctgccgcc acggttaaag acttatacga cctatcacaa tcaccgctga cctttacagg   2100
tgatagcggt aacgttaaga gaaaactggg tcagacttta accatcacag gcggacaaac   2160
aaagaccgat caattaaccg acaataacat cggtgtggta gcaggtacta atggcttaac   2220
cgttaaactt gctaaaactt taaacagtct tactgaagtt aatacggcta cattaaacgc   2280
caccaataaa gttaaggtag ataatagtac tggtaatacg gctgaattat aaacaatgg   2340
tttaaccttt acccaaacaa caggtgcaaa ttcaggtaaa accgtctatg caatgatgg    2400
cttgaagttt actaatagtg ctaataaagc acttggcggc acaacttaca tcaccaaaga   2460
tcaagttggt tttagcaatc aagatggctt acttgatgaa agcaaaccgt atcttaaccg   2520
agaaaagcta aaagttggta aaattgagat taaagacagt ggcattaatg caggtggtaa   2580
agccatcaca ggactgccct caacactgcc caacactacc tatactgcac ctggcgtgca   2640
tactgcacta catggcagta caattttctaa cgacgacaaa acccgtgccg ccagtatcgc   2700
cgatgtgcta aacgcaggct ttaacttgga aggtaatggt gaagcggttg actttgtctc   2760
```

```
cacttatgac accgtcaact ttgccgatgg caatgccacc accgctaagg taacttatga   2820
taacaaaacc agtaaagtgg cgtatgatgt caatgtggat ggtacaacca ttcatctaac   2880
aggcactaat ggcaagaaaa accaaattgg cgtaaaaacc accacactga ccacaaaacg   2940
tgctaaaggt aatacagcaa ctaattttag tgttaactct ggtgatgaca atgcccttat   3000
taacgccaaa gacatcgccg acaatctaaa caccctagct ggtgaaattc gcaccgccaa   3060
aggcacagca agcaccgccc tacaaacctt ctctattatt gatgaacaag gtaataactt   3120
tatggtcggt aaccttttact ctggttatga caccctcaaat acctctgaga ccgtcacctt   3180
tgtaggtgaa aacggcatta ccaccaaggt aaataaaggt aaagtcaaag ttggtattga   3240
ccaaaccaaa ggcttaacca cgcctaagct gaccgtgggt agtagtaatg gcaaaggcat   3300
tgtcattgac agtaaagatg gtcaaaatac catcacagga ctaagcaaca ctctaaccga   3360
tgccaccaac gcaacaacag gcatgtcag tgaaatccag ggcttggcac aaggtgcaaa   3420 caaaaccgt gccgccagca ttggtgatgt actaaacgca ggctttaact tgcaaggcaa   3480
tggtgaagcc aaagactttg tctccactta tgacaccgtc aactttatcg atggcaatgc   3540
caccaccgct aaggtgacct atgatgacac gaaacagacc agcacagtaa cttatgatgt   3600
caatgtggat aataaaaccc ttgaagtgac aggcgataaa aaacttggcg tcaaaaccac   3660
cacactgacc aaaacaagtg ctaatggtaa tgcaaccaaa tttagtgccg ccgatggcga   3720
tgcccttgtt aaagccagtg atatcgccac ccatctaaat accttggctg gcgacatcca   3780
aaccgccaaa ggagcaagcc aagcaagcag ctcagcaagc tatgtggatg ctgatggcaa   3840
caaggtcatc tatgacagta ccgataagaa gtactatcaa gccaaaaatg atggcacagt   3900
tgataaaacc aaagaagttg ccaaagacaa actggtcgcc caagcccaaa ccccagatgg   3960
cacattggct cgaatgaatg tcaaatcagt cattaacaaa gaacaagtaa atgatgccaa   4020
taaaaagcaa ggcatcaacg aagacaacgc ctttgttaaa ggacttgaaa agccgcttc   4080 tgataacaaa accaaaaacg ccgcagtaac tgtgggtgat ttaaatgccg ttgcccaaac   4140
accgctgacc tttgcagggg atacaggcac aacggctaaa aaactgggcg agactttgac   4200
catcaaaggt gggcaaacag acaccaataa gctaaccgat aataacatcg gtgtggtagc   4260
aggtactgat ggcttcactg tcaaacttgc caaagaccta accatcttta cagcgttaa   4320 tgcaggtggc accaaaattg atgacaaagg cgtgtctttt gtagacgcaa acggtcaagc   4380
caaagcaaac cccctgtgc taagtgccaa tgggctggac ctgggtggca acgcatcag   4440 taacatcggt gcagctgttg atgataacga tgcggtgaac tttaagcagt ttaatgaagt   4500
tgccaaaacg gtcaacaacc taaacaacca aagtaactca ggtgcgtcat tgcccttttgt   4560 agtaaccgat gccaatggca agcccatcaa tggcaccgat gacaagcccc aaaaagccat   4620
caagggcgcc gatggtaaat actatcacgc caacgccaac ggcgtacctg tggacaaaga   4680
tggcaacccc atcaccgatg cggacaaact tgccaatctg gcagctcatg gcaaacccct   4740
tgatgcaggt catcaagtgg tggcaagcct aggcggcaac tcagatgcca tcaccctaac   4800
caacatcaag tccactttgc cacaaattga cacaccaaac acaggtaatg ccaatgcagg   4860
gcaagcccaa agtctgccca gcctatcagc agcacagcaa agtaatgctg ccagtgtcaa   4920
agatgtgcta aatgtaggct ttaacttgca gaccaatcac aatcaagtgg actttgtcaa   4980
agcctatgat accgtcaact tgtcaatgg tacaggtgcc gacatcacaa gcgtgcgtag   5040
tgctgatggc acgatgagta acatcaccgt caacaccgcc ttagcagcga ccgatgatga   5100
```

-continued

```
tggcaatgtg cttatcaaag ccaaagatgg taagttctac aaagcagacg acctcatgcc    5160
aaacggctca ctaaaagcag gcaaatcagc cagtgatgcc aaaactccaa ctggtctaag    5220
ccttgtcaac cccaatgctg gtaaaggcag tacaggcgat gcagtggctc ttaataactt    5280
atcaaaagcg gtatttaaat ccaaagatgg tacaactact accacagtaa gctctgatgg    5340
catcagtatc caaggcaaag ataacagcaa catcaccta agcaaagatg ggctgaatgt    5400
aggcggtaag gtcatcagca atgtgggtaa aggcacaaaa gacaccgacg ctgccaatgt    5460
acaacagtta aaccgaagta cgcaacttgt tgggtcttgg gtaatggctg gtaatgataa    5520
cgctgacggc aatcaggtaa acattgccga catcaaaaaa gacccaaatt caggttcatc    5580
atctaaccgc actgtcatca aagcaggcac ggtacttggc ggtaaaggta ataacgatac    5640
cgaaaaactt gccactggtg gtgtacaagt gggcgtggat aaagacggca acgctaacgg    5700
cgatttaagc aatgtttggg tcaaaaccca aaaagatggc agcaaaaaag ccctgctcgc    5760
cacttataac gccgcaggtc agaccaacta tttgaccaac aaccccgcag aagccattga    5820
cagaataaat gaacaaggta tccgcttctt ccatgtcaac gatggcaatc aagagcctgt    5880
ggtacaaggg cgtaacggca ttgactcaag tgcctcaggc aagcactcag tggcggtcgg    5940
ttataaggcc aaggcagatg gtgaagccgc cgttgccata ggcagacaaa cccaagcagg    6000
caaccaatcc atcgccatcg gtgataacgc acaagccaca ggcgatcaat ccatcgccat    6060
cggtacaggc aatgtggtag caggtaagca ctctggtgcc atcggcgacc caagcactgt    6120
taaggctgat aacagttaca gtgtgggtaa taacaaccag tttaccgatg ccactcagac    6180
cgatgtcttt ggtgtgggca ataacatcac cgtgaccgaa agtaactcgg ttgccttagg    6240
ttcaaactct gccatcagtg caggcacaca cgcaggcaca caagccaaaa aatctgacgg    6300
cacagcaggt acaaccacca cagcaggtgc aacaggtacg gttaaaggct tgctggaca    6360 aacggcggtt ggtgcggtct ccgtgggtgc ctcaggtgct gaacgccgta tccaaaatgt    6420
ggcagcaggt gaggtcagtg ccaccagcac cgatgcggtc aatggtagcc agttgtacaa    6480
agccacccaa agcattgcca acgcaaccaa tgagcttgac catcgtatcc accaaaacga    6540
aaataaagcc aatgcaggga tttcatcagc gatggcgatg gcgtccatgc cacaagccta    6600
cattcctggc agatccatgg ttaccggggg tattgccacc cacaacggtc aaggtgcggt    6660
ggcagtggga ctgtcgaagc tgtcggataa tggtcaatgg gtatttaaaa tcaatggttc    6720
agccgatacc caaggccatg taggggcagc agttggtgca ggttttcact tttaagccat    6780
aaatcgcaag attttactta aaaatcaatc tcaccatagt tgtataaaac agcatcagca    6840
tcagtcatat tactgatgct tgatggtttt tattacttaa accatttta            6889
```

<210> SEQ ID NO 3
<211> LENGTH: 30
<212> TYPE: DNA
<213> ORGANISM: Moraxella catarrhalis

<400> SEQUENCE: 3

```
cgggatccga tggccgtggc ggaatatgcc                                     30
```

<210> SEQ ID NO 4
<211> LENGTH: 38
<212> TYPE: DNA
<213> ORGANISM: Moraxella catarrhalis

<400> SEQUENCE: 4

```
cgcggatccg aaaagtgaaa acctgcacca actgctgc                            38
```

<210> SEQ ID NO 5
<211> LENGTH: 38
<212> TYPE: DNA
<213> ORGANISM: Moraxella catarrhalis

<400> SEQUENCE: 5
tgtcagcatg tatcattttt ttaaggtaaa ccaccatg                        38

<210> SEQ ID NO 6
<211> LENGTH: 28
<212> TYPE: DNA
<213> ORGANISM: Moraxella catarrhalis

<400> SEQUENCE: 6
catcaattgc gatatgtctg ggatcttg                                   28

<210> SEQ ID NO 7
<211> LENGTH: 25
<212> TYPE: DNA
<213> ORGANISM: Moraxella catarrhalis

<400> SEQUENCE: 7
cttcacccca tcagtgccat agacc                                      25

<210> SEQ ID NO 8
<211> LENGTH: 150
<212> TYPE: PRT
<213> ORGANISM: Moraxella catarrhalis

<400> SEQUENCE: 8

Ala Leu His Gly Ser Thr Ile Ser Asn Asp Asp Lys Thr Arg Ala Ala
  1               5                  10                  15

Ser Ile Ala Asp Val Leu Asn Ala Gly Phe Asn Leu Glu Gly Asn Gly
                 20                  25                  30

Glu Ala Val Asp Phe Val Ser Thr Tyr Asp Thr Val Asn Phe Ala Asp
             35                  40                  45

Gly Asn Ala Thr Thr Ala Lys Val Thr Tyr Asp Asn Lys Thr Ser Lys
         50                  55                  60

Val Ala Tyr Asp Val Asn Val Asp Gly Thr Thr Ile His Leu Thr Gly
 65                  70                  75                  80

Thr Asn Gly Lys Lys Asn Gln Ile Gly Val Lys Thr Thr Thr Leu Thr
                 85                  90                  95

Thr Lys Arg Ala Lys Gly Asn Thr Ala Thr Asn Phe Ser Val Asn Ser
            100                 105                 110

Gly Asp Asp Asn Ala Leu Ile Asn Ala Lys Asp Ile Ala Asp Asn Leu
        115                 120                 125

Asn Thr Leu Ala Gly Glu Ile Arg Thr Ala Lys Gly Thr Ala Ser Thr
    130                 135                 140

Ala Leu Gln Thr Phe Ser
145                 150

<210> SEQ ID NO 9
<211> LENGTH: 450
<212> TYPE: DNA
<213> ORGANISM: Moraxella catarrhalis

<400> SEQUENCE: 9
gcactacatg gcagtacaat ttctaacgac gacaaaaccc gtgccgccag tatcgccgat    60

-continued

```
gtgctaaacg caggctttaa cttggaaggt aatggtgaag cggttgactt tgtctccact    120
tatgacaccg tcaactttgc cgatggcaat gccaccaccg ctaaggtaac ttatgataac    180
aaaaccagta aagtggcgta tgatgtcaat gtggatggta caaccattca tctaacaggc    240
actaatggca agaaaaacca aattggcgta aaaaccacca cactgaccac aaaacgtgct    300
aaaggtaata cagcaactaa ttttagtgtt aactctggtg atgacaatgc ccttattaac    360
gccaaagaca tcgccgacaa tctaaacacc ctagctggtg aaattcgcac cgccaaaggc    420
acagcaagca ccgccctaca aaccttctct                                     450
```

<210> SEQ ID NO 10
<211> LENGTH: 239
<212> TYPE: PRT
<213> ORGANISM: Moraxella catarrhalis

<400> SEQUENCE: 10

Asp Gln Thr Lys Gly Leu Thr Thr Pro Lys Leu Thr Val Gly Ser Ser
 1               5                  10                  15

Asn Gly Lys Gly Ile Val Ile Asp Ser Lys Asp Gly Gln Asn Thr Ile
                20                  25                  30

Thr Gly Leu Ser Asn Thr Leu Thr Asp Ala Thr Asn Ala Thr Thr Gly
            35                  40                  45

His Val Ser Glu Ile Gln Gly Leu Ala Gln Gly Ala Asn Lys Thr Arg
        50                  55                  60

Ala Ala Ser Ile Gly Asp Val Leu Asn Ala Gly Phe Asn Leu Gln Gly
    65                  70                  75                  80

Asn Gly Glu Ala Lys Asp Phe Val Ser Thr Tyr Asp Thr Val Asn Phe
                85                  90                  95

Ile Asp Gly Asn Ala Thr Thr Ala Lys Val Thr Tyr Asp Asp Thr Lys
               100                 105                 110

Gln Thr Ser Thr Val Thr Tyr Asp Val Asn Val Asp Asn Lys Thr Leu
           115                 120                 125

Glu Val Thr Gly Asp Lys Lys Leu Gly Val Lys Thr Thr Thr Leu Thr
       130                 135                 140

Lys Thr Ser Ala Asn Gly Asn Ala Thr Lys Phe Ser Ala Ala Asp Gly
145                 150                 155                 160

Asp Ala Leu Val Lys Ala Ser Asp Ile Ala Thr His Leu Asn Thr Leu
               165                 170                 175

Ala Gly Asp Ile Gln Thr Ala Lys Gly Ala Ser Gln Ala Ser Ser Ser
           180                 185                 190

Ala Ser Tyr Val Asp Ala Asp Gly Asn Lys Val Ile Tyr Asp Ser Thr
       195                 200                 205

Asp Lys Lys Tyr Tyr Gln Ala Lys Asn Asp Gly Thr Val Asp Lys Thr
   210                 215                 220

Lys Glu Val Ala Lys Asp Lys Leu Val Ala Gln Ala Gln Thr Pro
225                 230                 235

<210> SEQ ID NO 11
<211> LENGTH: 717
<212> TYPE: DNA
<213> ORGANISM: Moraxella catarrhalis

<400> SEQUENCE: 11

```
gaccaaacca aaggcttaac cacgcctaag ctgaccgtgg gtagtagtaa tggcaaaggc     60
attgtcattg acagtaaaga tggtcaaaat accatcacag gactaagcaa cactctaacc    120
```

```
gatgccacca acgcaacaac agggcatgtc agtgaaatcc agggcttggc acaaggtgca      180
aacaaaaccc gtgccgccag cattggtgat gtactaaacg caggctttaa cttgcaaggc      240
aatggtgaag ccaaagactt tgtctccact tatgacaccg tcaactttat cgatggcaat      300
gccaccaccg ctaaggtgac ctatgatgac acgaaacaga ccagcacagt aacttatgat      360
gtcaatgtgg ataataaaac ccttgaagtg acaggcgata aaaaacttgg cgtcaaaacc      420
accacactga ccaaaacaag tgctaatggt aatgcaacca aatttagtgc cgccgatggc      480
gatgcccttg ttaaagccag tgatatcgcc acccatctaa ataccttggc tggcgacatc      540
caaaccgcca aggagcaag ccaagcaagc agctcagcaa gctatgtgga tgctgatggc      600
aacaaggtca tctatgacag taccgataag aagtactatc aagccaaaaa tgatggcaca      660
gttgataaaa ccaagaagt tgccaaagac aaactggtcg cccaagccca aaccca         717
```